United States Patent
Ruers et al.

(10) Patent No.: US 10,753,862 B2
(45) Date of Patent: Aug. 25, 2020

(54) METHOD, APPARATUS AND SOFTWARE FOR DETECTION AND LOCALIZATION OF HIDDEN DEFECTS IN OPTICALLY DIFFUSE MEDIA

(71) Applicant: Stichting Het Nederlands Kanker Instituut-Antoni van Leeuwenhoek Ziekenhuis, Amsterdam (NL)

(72) Inventors: Theodoor Jacques Marie Ruers, Amsterdam (NL); Esther Kho, Amsterdam (NL); Henricus Josephus Cornelus Maria Sterenborg, Amsterdam (NL)

(73) Assignee: Stichting Het Nederlands Kanker Instituut-Antoni Van Leeuwenhoek Ziekenhuis, Amsterdam (NL)

( * ) Notice: Subject to any disclaimer, the term of this patent is extended or adjusted under 35 U.S.C. 154(b) by 0 days.

(21) Appl. No.: 16/077,768

(22) PCT Filed: Feb. 14, 2017

(86) PCT No.: PCT/NL2017/050086
§ 371 (c)(1),
(2) Date: Aug. 14, 2018

(87) PCT Pub. No.: WO2017/142399
PCT Pub. Date: Aug. 24, 2017

(65) Prior Publication Data
US 2019/0041319 A1 Feb. 7, 2019

(30) Foreign Application Priority Data

Feb. 16, 2016 (NL) .................................... 2016273
Nov. 2, 2016 (NL) .................................... 2017700

(51) Int. Cl.
*G01N 21/31* (2006.01)
*G01N 33/02* (2006.01)
(Continued)

(52) U.S. Cl.
CPC ......... *G01N 21/314* (2013.01); *A61B 5/0075* (2013.01); *A61B 5/441* (2013.01);
(Continued)

(58) Field of Classification Search
CPC .................................................. G01N 21/314
(Continued)

(56) References Cited

U.S. PATENT DOCUMENTS 6,061,583 A * 5/2000 Ishihara ............. A61B 5/14535
600/322
6,075,610 A * 6/2000 Ueda ...................... G01N 21/49
356/343

(Continued)

*Primary Examiner* — Tarifur R Chowdhury
*Assistant Examiner* — Omar H Nixon
(74) *Attorney, Agent, or Firm* — Hoffmann & Baron, LLP

(57) ABSTRACT

In a method and apparatus, a property of an optically diffuse medium including a first optical absorber having a first concentration and a second optical absorber having a second concentration is determined. A surface area of the medium is imaged at multiple wavelengths around an isosbestic wavelength of the first absorber and the second absorber. A reflectance spectrum of the medium at the surface area at the multiple wavelengths is determined. A derivative of the determined reflectance spectrum around the isosbestic wavelength is determined. From the derivative, a concentration ratio of the first concentration and the second concentration is estimated.

33 Claims, 12 Drawing Sheets

(51) Int. Cl.
*G01N 33/12* (2006.01)
*G01N 21/47* (2006.01)
*G01N 21/49* (2006.01)
*A61B 5/00* (2006.01)
*G01J 3/42* (2006.01)
*G01J 3/28* (2006.01)
*G01J 3/12* (2006.01)

(52) U.S. Cl.
CPC .......... *A61B 5/4869* (2013.01); *A61B 5/4872* (2013.01); *A61B 5/4875* (2013.01); *G01J 3/2823* (2013.01); *G01J 3/42* (2013.01); *G01N 21/4738* (2013.01); *G01N 21/4795* (2013.01); *G01N 21/49* (2013.01); *G01N 33/02* (2013.01); *G01N 33/025* (2013.01); *G01N 33/12* (2013.01); *A61B 5/0077* (2013.01); *A61B 5/0091* (2013.01); *A61B 5/7239* (2013.01); *A61B 2505/05* (2013.01); *A61B 2576/00* (2013.01); *G01J 2003/1213* (2013.01); *G01J 2003/1221* (2013.01); *G01J 2003/2826* (2013.01); *G01J 2003/425* (2013.01); *G01N 2021/3133* (2013.01); *G01N 2021/3137* (2013.01); *G01N 2021/3174* (2013.01); *G01N 2201/103* (2013.01); *G01N 2201/1053* (2013.01)

(58) Field of Classification Search
USPC ......................................................... 356/314
See application file for complete search history.

(56) References Cited

U.S. PATENT DOCUMENTS

| | | | | |
|---|---|---|---|---|
| 6,335,792 | B1* | 1/2002 | Tsuchiya | G01N 21/4795 356/343 |
| 2003/0139886 | A1* | 7/2003 | Bodzin | G01N 21/47 702/28 |
| 2003/0208111 | A1 | 11/2003 | Mattu et al. | |
| 2005/0273011 | A1 | 12/2005 | Hattery et al. | |
| 2006/0188407 | A1* | 8/2006 | Gable | A61B 5/0084 604/19 |
| 2008/0199080 | A1 | 8/2008 | Subbiah et al. | |
| 2010/0076281 | A1* | 3/2010 | Navon | A61B 5/14535 600/323 |
| 2013/0102865 | A1* | 4/2013 | Mandelis | A61B 5/0095 600/328 |
| 2015/0132789 | A1* | 5/2015 | Bornheimer | G01J 3/42 435/29 |
| 2015/0164347 | A1* | 6/2015 | Pollonini | A61B 5/0261 600/323 |
| 2016/0058274 | A1* | 3/2016 | Chiba | G01N 21/314 600/328 |
| 2016/0146723 | A1* | 5/2016 | Chiba | A61B 1/00009 250/208.1 |

* cited by examiner

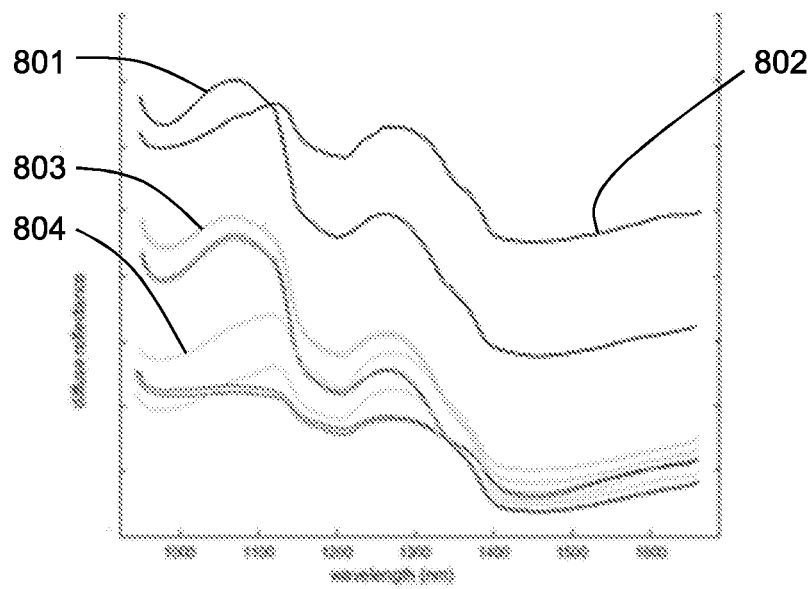
FIG. 8a
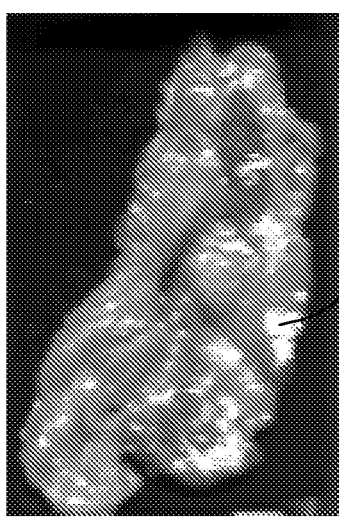 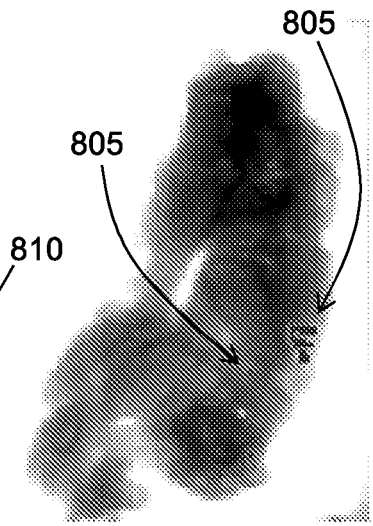 
FIG. 8b   FIG. 8c   FIG. 8d

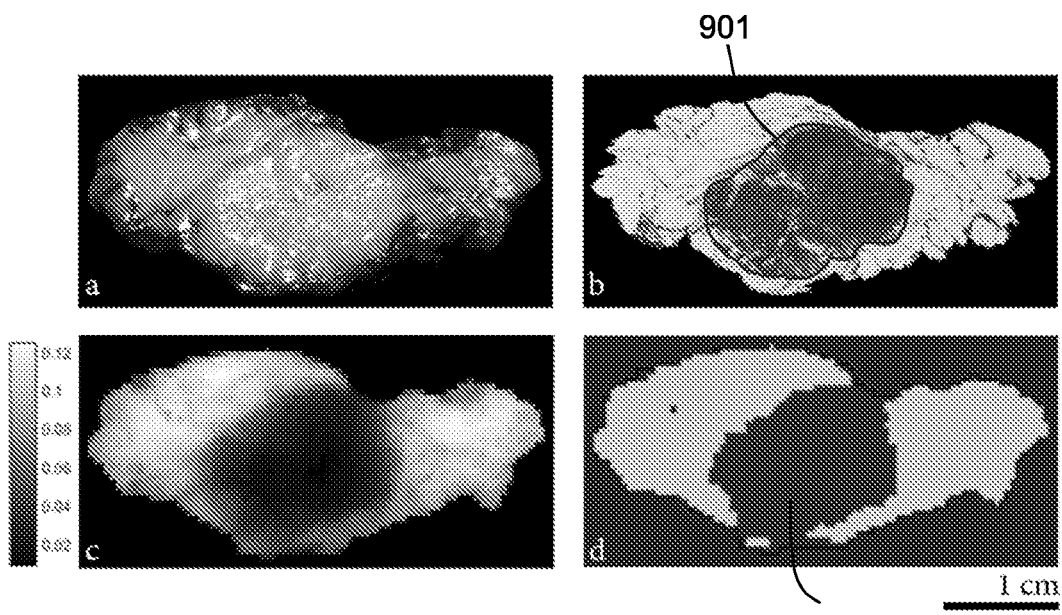
FIG. 9a-d
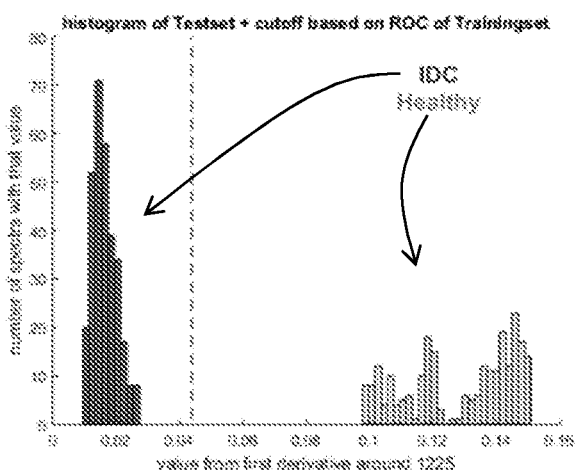 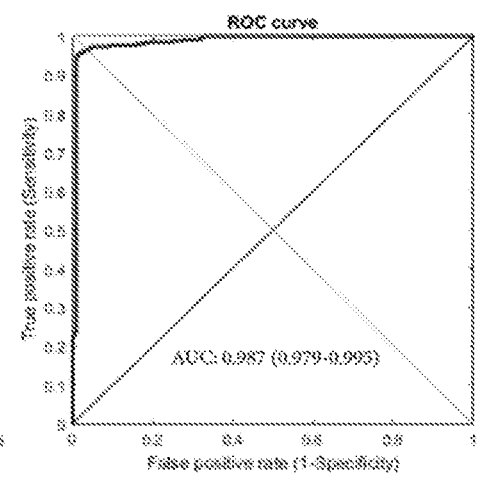
FIG. 9e          FIG. 9f

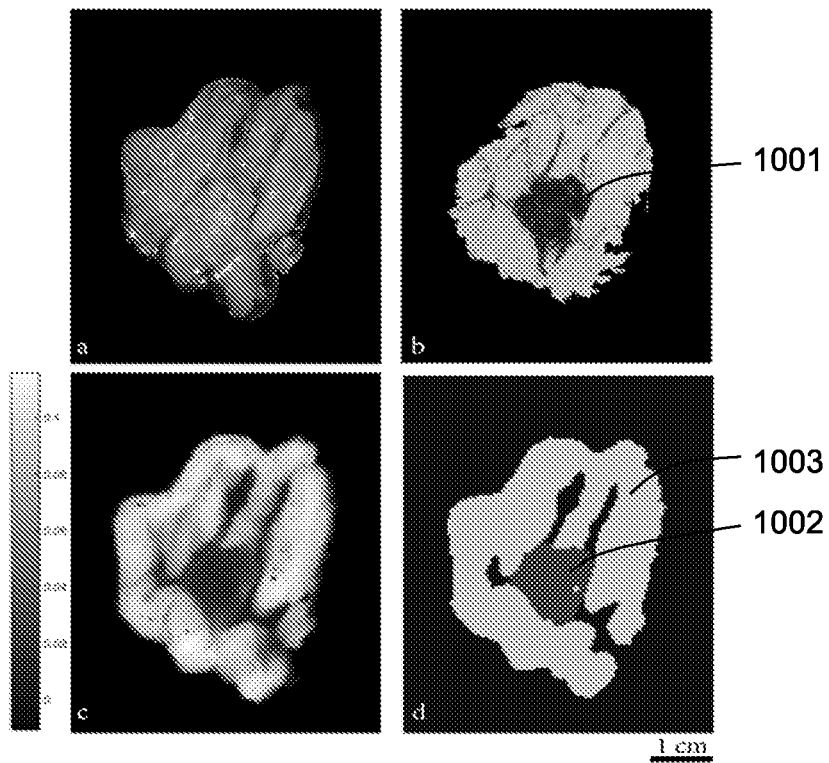
FIG. 10a-d
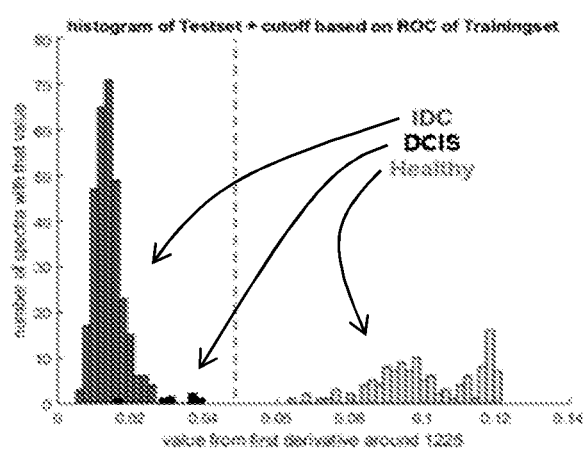
FIG. 10e
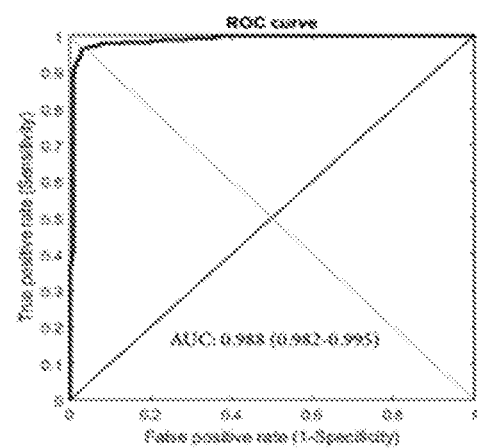
FIG. 10f

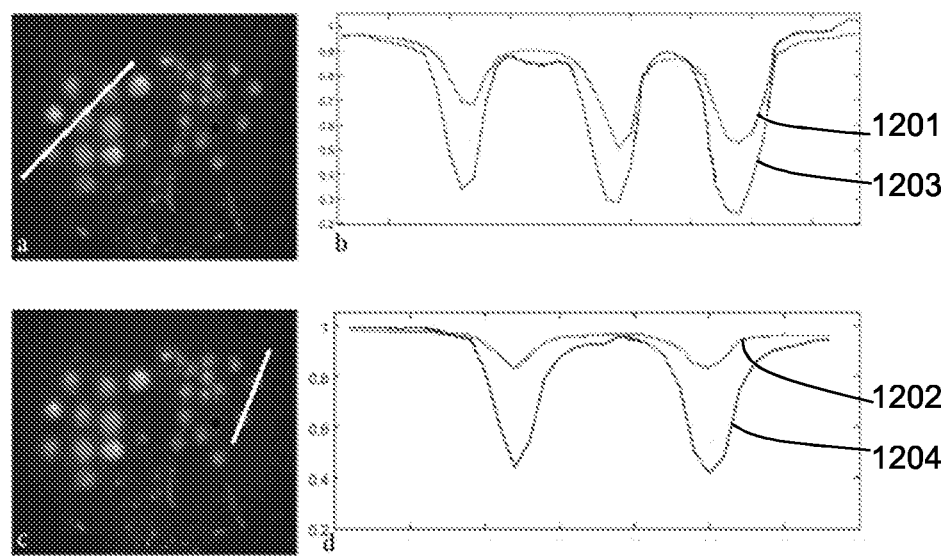
FIG. 12a-d

METHOD, APPARATUS AND SOFTWARE FOR DETECTION AND LOCALIZATION OF HIDDEN DEFECTS IN OPTICALLY DIFFUSE MEDIA

CROSS-REFERENCE TO RELATED APPLICATIONS

This application is the National Stage of International Application No. PCT/NL2017/050086, filed Feb. 14, 2017, which claims the benefit of Netherlands Application Nos. NL 2016273, filed Feb. 16, 2016, and NL 2017700, filed Nov. 2, 2016, the contents of all of which are incorporated by reference herein.

FIELD OF THE INVENTION

The invention relates to optical imaging of highly scattering media. In particular, this invention relates to optical imaging of optically diffuse biological materials, or media, for detecting and locating damage, disease and/or (defects in) anatomic structure. This damage, disease and (defects in) anatomic structure may be hidden, i.e. poorly visible or invisible to the human eye.

BACKGROUND OF THE INVENTION

Visual inspection is the oldest technique available to mankind to assess the quality of biological materials such as fruits, vegetables, meat, fish and live human tissue. Moreover, until recently, visual inspection has been the only technique available to mankind to assess the health status of said biological materials from the outer surface thereof.

Recently, camera based optical imaging has made its entry into the medical field. The power of optical imaging lies in the phenomenon that light penetrates up to centimeters into many biological materials. In most of these materials light is scattered strongly and becomes diffuse. In addition, very specific wavelengths of light are absorbed by specific tissue components.

Together, absorption and scattering determine the amount and spectral distribution of the light that is reflected. Hence, diffuse optical images do not only give information on the shape and the surface of the material imaged, but more importantly on what is below the surface.

Depending on the wavelength of the light, sampling depths in the order of, or up to, a centimeter, cm, are feasible.

In multispectral or hyperspectral imaging, optical images are acquired using dedicated camera systems that detect light in different wavelength bands. The images taken by these cameras are often processed by various image processing methods to obtain information on the status of biochemical composition of the imaged object. Examples of materials subjected to diffuse optical imaging range from raw foods to assess their freshness, crops to assess their status, to live human tissues to detect and locate remaining cancer cells during and after surgery.

Although light scattering is the very phenomenon that enables diffuse optical imaging, it also complicates quantitatively accurate imaging, and it limits the sharpness of the images taken.

When imaging a homogenous medium, the diffuse light captured in the form of diffuse reflection gives an excellent representation of the optical properties of the tissue. If images are taken at sufficient wavelengths, then there are ample mathematical models available that allow spectral unmixing, i.e. the extraction of the different concentrations of the tissue components.

These methods vary from complicated diffusion theory based spectral analyses based on a lot of prior knowledge on light transport and the tissue components to purely mathematical techniques such as spectral unmixing, SU, or machine learning, ML. Often, more simple approaches are used such as ratioing the diffuse reflectance at two strategically chosen wavelengths.

Preferentially, however, diffuse optical imaging is used in cases where a defect is not spread over the tissue evenly, and its location is not known. In fact, the purpose of imaging usually is to detect and locate a defect. In such a case the diffuse nature of the reflected light limits the sharpness of the image, and thereby decreases the accuracy of detection of small defects.

In diffuse media, the sampling depth and imaging resolution are inversely related: in the case of a decreased scattering coefficient the diffuse light detected has sampled deeper into the tissue, generating an image with a lower spatial resolution, while a sample with a larger scattering coefficient samples more superficially and may have a higher spatial resolution.

A case of inhomogeneously distributed optical properties is not rare, since most biological materials are very inhomogeneous. A possible defect can be considered as an additional inhomogeneity. For diffuse light this has serious consequences as the diffuse light will encounter different optical properties at different locations. Because these optical properties are wavelength dependent and this wavelength dependence is different for different tissue compositions, the diffuse light will have different distributions at different wavelengths.

As a consequence, different wavelengths will sample different volumes. This will compromise any spectral unmixing approach. This phenomenon is very well known in the field of diffuse optical spectroscopy.

In many cases, simple ratios of images taken at strategically chosen wavelengths can give excellent information on the ratio between different absorbing components. These numbers can then be used to characterize the tissue.

As an example, a fat-to-water ratio image has been proposed to be of particular interest, in particular for a diagnosis of breast cancer. Such a ratio would be accurate in homogenous tissue. Due to the inhomogeneous nature of the distributions of these tissue components, the ratios calculated have been documented to be in error by as much as 50%.

For a medium, the diffuse reflection $R_d$ can be related to the absorption coefficient by the relation:

$$R_d \sim e^{-\mu_a \langle l \rangle} \quad (1.1)$$

where $\mu_a$ stands for the absorption coefficient and $\langle l \rangle$ for the average path length of the detected photons.

When taking two wavelengths $\lambda_1$ and $\lambda_2$, a ratio X can be calculated from the natural logs of the diffuse reflections:

$$X = \frac{\langle l_2 \rangle \mu_a(\lambda_2)}{\langle l_1 \rangle \mu_a(\lambda_1)} = \frac{\ln(R_d(\lambda_2))}{\ln(R_d(\lambda_1))} \quad (1.2)$$

Assuming the presence of two absorbers at molar concentrations $C_1$ and $C_2$, then:

$$\mu_a(\lambda) = C_1 \mu_{a,1}(\lambda) + C_2 \mu_{a,2}(\lambda) \quad (1.3)$$

where $\mu_{a,m}(\lambda)$ stands for the molar absorption coefficient of absorber with index m. Introducing the concentration ratio:

$$\psi = \frac{C_1}{C_1 + C_2} \quad (1.4)$$

so that (1.3) can be written as:

$$\mu_a(\lambda) = (C_1 + C_2)(\psi \mu_{a,1}(\lambda) + (1-\psi)\mu_{a,2}(\lambda)) \quad (1.5)$$

Now expression (1.2) can be rewritten into:

$$X = \frac{\ln(R_d(\lambda_2))}{\ln(R_d(\lambda_1))} = \frac{\langle l_1 \rangle}{\langle l_2 \rangle} \left( \frac{\psi \mu_{a,1}(\lambda_2) + (1-\psi)\mu_{a,2}(\lambda_2)}{\psi \mu_{a,1}(\lambda_1) + (1-\psi)\mu_{a,2}(\lambda_1)} \right) \quad (1.6)$$

From expression (1.6) it is clear that, when the path lengths $\langle l_1 \rangle$ and $\langle l_2 \rangle$ are identical and the absorption properties of both absorbers are known, the concentration ratio $\psi$ can be derived from the ratio of the natural logarithms of the reflectances. The strongest sensitivity is found when wavelengths $\lambda_1$ and $\lambda_2$ are chosen to be at wavelengths where the two absorbers have maximum differences. This ratio is often used in hyper or multi spectral imaging to quantify concentration ratios of chromophores.

The main problem in practical application of expression (1.6), lies in the assumption that $\langle l_1 \rangle = \langle l_2 \rangle$. In practice the path lengths, $\langle l_1 \rangle$ and $\langle l_2 \rangle$, are dependent on the optical properties.

There are three main reasons why the assumption $\langle l_1 \rangle = \langle l_2 \rangle$ is problematic in practical use.

A first reason is that the path length is dependent on both the absorption and the scattering properties. When aiming at a maximum sensitivity, the wavelengths $\lambda_1$ and $\lambda_2$ are chosen to be at wavelengths where the two absorbers have maximum differences. This results in very different path lengths and sampling volumes, even in homogeneous tissue.

A second reason is that the two tissue types with different concentrations of the two absorbers considered may be biologically very different. Hence it is likely that these tissues will also have very different scattering properties. This too causes large differences in path lengths and hence differences in sampling volumes.

A third reason is that the need for imaging implies inhomogeneous tissue, where different types of tissue with very different optical properties coexist. This results in very different path lengths and very different sampling volumes in the different tissue areas. Also it can generate artefacts in the boundary region between the two tissues. Detected photons show a preference for 'paths of lowest absorption': Light detected at the wavelength of maximum absorption of a first absorber will have a stronger contribution from photons that have travelled preferentially through tissue containing a higher concentration of a second absorber, and vice versa. So, even if $\langle l_1 \rangle$ would be of the same length as $\langle l_2 \rangle$, the two paths would have sampled very different tissue volumes. This problem leads to an overestimation of the total amount of tissue components.

SUMMARY OF THE INVENTION

It would be desirable to provide a method and apparatus for optically imaging a spatial distribution of the ratio of concentrations of optical absorbers comprised in a medium. It would also be desirable to more accurately perform said optical imaging.

It would further be desirable to provide a method and device to optimize the spatial resolution in said imaging method.

To better address one or more of these concerns, in a first aspect of the invention a method of determining a property of an optically diffuse medium is provided. The medium comprises a first optical absorber having a first concentration and a second optical absorber having a second concentration. The method comprises the steps of:

(a) imaging a surface area of a volume of the medium at multiple wavelengths around an isosbestic wavelength of the first absorber and the second absorber;

(b) determining a reflectance spectrum of the medium at the surface area at the multiple wavelengths;

(c) determining a derivative of the determined reflectance spectrum around the isosbestic wavelength; and (c) estimating a concentration ratio of the first concentration and the second concentration from the derivative.

The invention is based on the approach that if there are problems due to differences in optical properties, then wavelengths should be used where the optical properties, in particular the optical path lengths are identical. Hereby, variations in sampling volume caused by differences in optical properties at the imaging wavelengths can be prevented.

A meaningful image can still be created when using such wavelengths, as explained below.

As no expression is available for the optical path length, the optical penetration depth, $\delta$, is looked into, defined as:

$$\langle l \rangle = 2\delta = \frac{2}{\sqrt{3\mu_a \mu'_s}} \quad (1.7)$$

wherein $\mu'_s$ is a reduced scattering coefficient. Expression (1.6) can be rewritten as:

$$X = \frac{\ln(R_d(\lambda_2))}{\ln(R_d(\lambda_1))} = \frac{\mu_a(\lambda_2)}{\mu_a(\lambda_1)} \sqrt{\frac{\mu_a(\lambda_1)\mu'_s(\lambda_1)}{\mu_a(\lambda_2)\mu'_s(\lambda_2)}} = \sqrt{\frac{\mu_a(\lambda_2)\mu'_s(\lambda_1)}{\mu_a(\lambda_1)\mu'_s(\lambda_2)}} \quad (1.8)$$

A path length corrected absorption ratio can now be calculated with:

$$\left( \frac{\psi \mu_{a,1}(\lambda_2) + (1-\psi)\mu_{a,2}(\lambda_2)}{\psi \mu_{a,1}(\lambda_1) + (1-\psi)\mu_{a,2}(\lambda_1)} \right) = \frac{\mu'_s(\lambda_2)}{\mu'_s(\lambda_1)} X^2 \quad (1.9)$$

This clearly illustrates a part of the problem: to obtain $\psi$ from X, the ratio of the scattering coefficients $$\frac{\mu'_s(\lambda_2)}{\mu'_s(\lambda_1)}$$

needs to be known.

Now a wavelength, $\lambda_0$, is looked for, for which the two tissues, first and second optical absorbers, have identical path lengths at the two wavelengths. This ensures that photons at both wavelengths do not see any differences between the two tissues and cannot do anything else than sampling the same volume.

The question, however, is that if the photons cannot 'see' differences between the tissues, how any differences can be imaged, i.e., the consequence of such a choice would be that at every concentration ratio the ratio X would be equal to 1.

Therefore, concentration ratios are obtained from the differences in shapes of the diffuse reflection spectra, by looking at the first or higher derivatives of the diffuse reflectance with respect to the wavelength measured closely around wavelengths that generate identical path lengths.

An imaging ratio DX is defined by subtracting two images taken $\Delta\lambda$ apart from a central wavelength $\lambda_0$ and dividing by the sum of the two images:

$$DX \equiv \frac{\ln((R_d(\lambda_0 + \Delta\lambda))) - \ln((R_d(\lambda_0 - \Delta\lambda)))}{\ln((R_d(\lambda_0 + \Delta\lambda))) + \ln((R_d(\lambda_0 - \Delta\lambda)))} \quad (1.10)$$

Because $\Delta\lambda$ is taken small with respect to $\lambda_0$, $R_d(\lambda)$ around $\lambda_0$ can be linearized, so that:

$$DX = \frac{\ln((R_d(\lambda_0 + \Delta\lambda))) - \ln((R_d(\lambda_0 - \Delta\lambda)))}{2\ln((R_d(\lambda_0)))} \quad (1.11)$$

This can be worked into $$DX = \frac{1}{2}\left(\frac{\ln((R_d(\lambda_0 + \Delta\lambda)))}{\ln(R_d(\lambda_0))} - \frac{\ln((R_d(\lambda_0 - \Delta\lambda)))}{\ln(R_d(\lambda_0))}\right) \quad (1.12)$$

Using a linear expansion of $\mu_a(\lambda)$ around $\lambda_0$:

$$DX = \quad (1.13)$$

$$\frac{1}{2}\left(\frac{\langle l_{\lambda_0+\Delta\lambda}\rangle}{\langle l_{\lambda_0}\rangle}\frac{\mu_a(\lambda_0) + \Delta\lambda\frac{\partial\mu_a}{\partial\lambda}\big|_{\lambda_0}}{\mu_a(\lambda_0)} - \frac{\langle l_{\lambda_0-\Delta\lambda}\rangle}{\langle l_{\lambda_0}\rangle}\frac{\mu_a(\lambda_0) - \Delta\lambda\frac{\partial\mu_a}{\partial\lambda}\big|_{\lambda_0}}{\mu_a(\lambda_0)}\right)$$

Rearranging:

$$DX = \frac{\langle l_{\lambda_0+\Delta\lambda}\rangle - \langle l_{\lambda_0-\Delta\lambda}\rangle}{2\langle l_{\lambda_0}\rangle} + \frac{\Delta\lambda\frac{\partial\mu_a}{\partial\lambda}\big|_{\lambda_0}}{\mu_a(\lambda_0)}\left(\frac{\langle l_{\lambda_0+\Delta\lambda}\rangle + \langle l_{\lambda_0-\Delta\lambda}\rangle}{2\langle l_{\lambda_0}\rangle}\right) \quad (1.14)$$

leads to:

$$DX = \frac{\Delta\lambda\frac{\partial\langle l_{\lambda_0}\rangle}{\partial\lambda}\big|_{\lambda_0}}{\langle l_{\lambda_0}\rangle} + \frac{\Delta\lambda\frac{\partial\mu_a}{\partial\lambda}\big|_{\lambda_0}}{\mu_a(\lambda_0)} \quad (1.15)$$

Approximating $\langle l_\lambda \rangle$ according to expression (1.7) yields:

$$\frac{\Delta\lambda\frac{\partial\langle l_{\lambda_0}\rangle}{\partial\lambda}\big|_{\lambda_0}}{\langle l_{\lambda_0}\rangle} = -\frac{\Delta\lambda}{2}\left(\frac{\frac{\partial\mu_a}{\partial\lambda}\big|_{\lambda_0}}{\mu_a(\lambda_0)} + \frac{\frac{\partial\mu_s'}{\partial\lambda}\big|_{\lambda_0}}{\mu_s'(\lambda_0)}\right) \quad (1.16)$$

which leads to:

$$DX = -\frac{\Delta\lambda}{2}\left(\frac{\frac{\partial\mu_a}{\partial\lambda}\big|_{\lambda_0}}{\mu_a(\lambda_0)} + \frac{\frac{\partial\mu_s'}{\partial\lambda}\big|_{\lambda_0}}{\mu_s'(\lambda_0)}\right) + \Delta\lambda\frac{\frac{\partial\mu_a}{\partial\lambda}\big|_{\lambda_0}}{\mu_a(\lambda_0)} \quad (1.17)$$

Thus:

$$DX = \frac{\Delta\lambda}{2}\left(\frac{\frac{\partial\mu_a}{\partial\lambda}\big|_{\lambda_0}}{\mu_a(\lambda_0)} - \frac{\frac{\partial\mu_s'}{\partial\lambda}\big|_{\lambda_0}}{\mu_s'(\lambda_0)}\right) \quad (1.18)$$

Differentiating expression (1.5) versus $\lambda$ yields:

$$\frac{\partial\mu_a}{\partial\lambda}\bigg|_{\lambda_0} = (C_1 + C_2)\left(\psi\frac{\partial\mu_{a,1}}{\partial\lambda}\bigg|_{\lambda_0} + (1-\psi)\frac{\partial\mu_{a,2}}{\partial\lambda}\bigg|_{\lambda_0}\right) \quad (1.19)$$

Before $\psi$ can be solved from expression (1.19) some strategic choices are made. First, wavelengths for which the absorption spectra of the two absorbers have an isosbestic point are considered. From expression (1.5) it is derived:

$$\mu_a(\lambda_0) = (C_1+C_2)\mu_{a,1}(\lambda_0) = (C_1+C_2)\mu_{a,2}(\lambda_0) = (C_1+C_2)\mu_{a,0} \quad (1.20)$$

Where $\lambda_0$ stands for the wavelength at which the two molar absorption coefficients $\mu_{a,1}(\lambda_0)$ and $\mu_{a,2}(\lambda_0)$ are identical. Now expression (1.16) turns into:

$$DX = \frac{\Delta\lambda}{2}\left(\frac{\left(\psi\frac{\partial\mu_{a,1}}{\partial\lambda}\big|_{\lambda_0} + (1-\psi)\frac{\partial\mu_{a,2}}{\partial\lambda}\big|_{\lambda_0}\right)}{\mu_{a,0}} - \frac{\frac{\partial\mu_s'}{\partial\lambda}\big|_{\lambda_0}}{\mu_s'(\lambda_0)}\right) \quad (1.21)$$

The first term in expression (1.21) has a linear dependence on $\psi$ with constants that are related to the first derivative of the absorption spectra. Thus, the ratio image defined in expression (1.21) can be directly interpreted in terms of $\psi$ if the absorption spectra of the two absorbers are known and sufficiently different in shape. Obviously, the ratio increases with increasing $\Delta\lambda$. Taking $\Delta\lambda$ too large will induce deviations from the premise that $\mu_a$ is constant. The order of magnitude of the first term depends on the steepness of the absorption curves. A simple estimate can be by considering a Gaussian absorption profile with bandwidth $\lambda_w$:

$$\mu_a(\lambda) = ae^{\left(-\frac{(\lambda-\lambda_c)^2}{2\lambda_w^2}\right)} \quad (1.22)$$

where $\lambda_c$ and $\lambda_w$ stand for the central wavelength and the half bandwidth, respectively.

Now an estimate for the first term in expression (1.18) can be derived:

$$\frac{\Delta\lambda}{2}\frac{\frac{\partial\mu_a}{\partial\lambda}}{\mu_a(\lambda_0)} = \frac{\Delta\lambda}{2}\frac{-\frac{\lambda-\lambda_c}{\lambda_w^2}ae^{\left(-\frac{(\lambda-\lambda_c)^2}{2\lambda_w^2}\right)}}{ae^{\left(-\frac{(\lambda-\lambda_c)^2}{2\lambda_w^2}\right)}} = -\frac{\Delta\lambda}{2}\frac{\lambda-\lambda_c}{\lambda_w^2} \quad (1.23)$$

At the steepest point of the absorption curve, i.e. $\lambda - \lambda_c$ equals $\pm \lambda_w$. In case the isosbestic point $\lambda_0$ lies anywhere near the absorption band this turns into:

$$\frac{\Delta\lambda}{2} \frac{\frac{\partial \mu_a}{\partial \lambda}}{\mu_a(\lambda_0)} \approx \pm \frac{\Delta\lambda}{2\lambda_w} \quad (1.24)$$

The second term has a more complicated behaviour. It describes the relative change in scattering coefficient with wavelength. In the case of Mie scatter:

$$\mu_s(\lambda) = \mu_s(\lambda_0)\left(\frac{\lambda}{\lambda_0}\right)^b \quad (1.26)$$

The second term in expression (1.18) simply becomes:

$$\frac{\Delta\lambda}{2} \frac{\frac{\partial \mu_s'}{\partial \lambda}\big|_{\lambda_0}}{\mu_s'(\lambda_0)} = \frac{\Delta\lambda}{2} \frac{\frac{b}{\lambda_0}\mu_s(\lambda_0)\left(\frac{\lambda}{\lambda_0}\right)^{b-1}}{\mu_s(\lambda_0)\left(\frac{\lambda}{\lambda_0}\right)^b} = \frac{\Delta\lambda}{\lambda}\frac{b}{2} \quad (1.27)$$

It is important to note that this is independent of the amount of scattering. It can be seen that the first term is much larger than the second term:

$$\frac{\Delta\lambda}{2\lambda_w} \gg \frac{\Delta\lambda}{\lambda}\frac{b}{2}, \text{ or } \frac{\lambda_0}{\lambda_w} \gg b \quad (1.28)$$

While values for b for most tissues are in the range from 0.5 to 2.0 and typical valuea for $\lambda_w$ and $\lambda_0$ of 40 nm and 1000 nm it is clear that the requirement of expressions (1.28) is fulfilled and that the first term in expression (1.18) is much bigger than the second term. An estimation of the concentration ratio $\psi$ can now with sufficiently high accuracy be calculated from:

$$= \frac{\frac{2DX}{\Delta\lambda} - g}{f - g} \cdot \psi = \frac{\frac{2DX}{\Delta\lambda} - \frac{\frac{\partial \mu_{a,2}}{\partial \lambda}\big|_{\lambda_0}}{\mu_{a,0}}}{\frac{\frac{\partial \mu_{a,1}}{\partial \lambda}\big|_{\lambda_0}}{\mu_{a,0}} - \frac{\frac{\partial \mu_{a,2}}{\partial \lambda}\big|_{\lambda_0}}{\mu_{a,0}}} \quad (1.29)$$

where the constants f and g are the relative derivatives of the two absorbers defined by expressions (1.30):

$$f = \frac{\frac{\partial \mu_{a,1}}{\partial \lambda}\big|_{\lambda_0}}{\mu_{a,0}} \text{ and } g = \frac{\frac{\partial \mu_{a,2}}{\partial \lambda}\big|_{\lambda_0}}{\mu_{a,0}}, \quad (1.30)$$

and where:
$\lambda$ indicates a wavelength;
$\lambda_0$ indicates an isosbestic wavelength;
$\Delta\lambda$ indicates a wavelength difference from the isosbestic wavelength;

DX indicates an imaging ratio, defined by subtracting two images taken $\Delta\lambda$ apart from an isosbestic wavelength $\lambda_0$ and dividing by the sum of the two images;
$\mu_{a,m}$ indicates a molar absorption coefficient of absorber m;
$\mu_{a,0}$ indicates a molar absorption coefficient at isosbestic wavelength.

Thus, the concentration ratio ($\psi$) may be determined using the partial derivative of a first molar absorption coefficient of the first absorber as a function of the wavelength, and the partial derivative of a second molar absorption coefficient of the second absorber as a function of the wavelength, both taken at a wavelength at which the first molar absorption coefficient and the second molar absorption coefficient are equal.

Instead of, or in addition to, the first derivative used here, similar considerations as the ones above may be applied to estimate the concentration ratio $\psi$, based on the use of second or higher derivatives. However, it is noted that the signal to noise ratio decreases substantially for the second or higher derivatives, which makes it at least less effective to use the second or higher derivatives.

In an embodiment, the method of the invention further comprises the steps of comparing the concentration ratio $\psi$ to a predetermined concentration ratio range, and indicating a defect for the surface area when the concentration ratio is outside the concentration ratio range.

For various media, in particular media comprised of, or comprising, living tissue, a concentration ratio of a first absorber and a second absorber in healthy tissue differs, often substantially, from a concentration ratio of unhealthy tissue. As an example, in mammal breast tissue, normal tissue has a lower fat to water ratio than cancer tissue. Now, by defining a concentration ratio range applicable to normal tissue, cancer tissue may be detected from its higher fat to water ratio, outside the concentration ratio range.

Accordingly, for one or more surface areas the concentration ratio may be determined, and when a defect is indicated for at least one surface area, an indication of a defect may be provided for the totality of surface areas. For example, an indication may be provided in an image of a plurality of surface areas, by colouring any surface area in which the concentration ratio is outside the concentration ratio range differently than other surface areas. From the image, a location and extension of cancer tissue may be recognized.

In an embodiment, the method of the invention further comprises the steps of repeating steps (a) to (d) for different isosbestic wavelengths of the first absorber and the second absorber in different wavelength regions to obtain estimated concentration ratios for each one of the isosbestic wavelengths.

Over a large range of wavelengths, there will often be several wavelength regions containing one or more isosbestic wavelengths where the optical penetration depth is independent of the ratio of the absorbers. The optical penetration depths in different wavelength regions can vary from a few centimetre to less than a millimetre. By performing the first and higher derivative imaging around isosbestic wavelengths in different wavelength regions, the optical penetration depth (sampling depth), and thereby the sampling volume of the imaging method can be changed.

In an embodiment, the method of the invention with repeating performing steps (a) to (d) for different isosbestic wavelengths further comprises comparing each one of the estimated concentration ratios to a predetermined concentration ratio range, and indicating a defect for the surface area when at least one of the concentration ratios is outside the concentration ratio range.

In an embodiment, the method of the invention with repeating performing steps (a) to (d) for different isosbestic wavelengths further comprises associating each isosbestic wavelength with a respective optical penetration depth, and indicating a defect and a depth thereof for the surface area if at least one of the concentration ratios is outside the concentration ratio range.

Thus, the method allows for providing not only indications of defects for surface areas, i.e. in two dimensions, but also for providing indications of the defects for sampling volumes, i.e. in three dimensions including a volume located beneath the imaged surface area.

In an embodiment, the method of the invention further comprises associating each isosbestic wavelength with a respective optical penetration depth, and, if small defects are to be located, selecting an isosbestic wavelength among the different isosbestic wavelengths with a low optical penetration depth.

By changing isosbestic wavelengths, not only the optical penetration depth is changed, but also the spatial resolution. A relatively high optical penetration depth is associated with a relatively low spatial resolution, and a relatively low optical penetration depth is associated with a relatively high spatial resolution. Thus, if particular sensitivity to small defects is required, a wavelength region with relatively low optical penetration depth is selected, to obtain a higher spatial resolution and hence a lower threshold for detection.

In a second aspect of the invention, an apparatus for determining a property of an optically diffuse medium is provided. The medium comprises a first optical absorber having a first concentration and a second optical absorber having a second concentration. The apparatus comprises:

a light source configured to illuminate a surface area of a volume of the medium;

a filtering device configured to receive reflected light from the surface area of the medium and to transmit filtered light to an optical imaging device, wherein the filtering device is configured to filter multiple wavelengths around an isosbestic wavelength of the first absorber and the second absorber;

a twodimensional, 2D, optical imaging device configured to receive the filtered light from the filtering device;

an image processing component configured to determine a reflectance spectrum of the medium at the surface area at the multiple wavelengths;

a calculating component configured to determine a derivative of the determined reflectance spectrum around the isosbestic wavelength; and an estimating component configured to estimate a concentration ratio of the first concentration and the second concentration from the derivative.

In a third aspect of the invention, an apparatus for determining a property of an optically diffuse medium is provided. The medium comprises a first optical absorber having a first concentration and a second optical absorber having a second concentration. The apparatus comprises:

a light source configured to illuminate a surface area of a volume of the medium;

a onedimensional, 1D, or twodimensional, 2D, hyperspectral optical imaging device configured to receive reflected light from the surface area of the medium;

an image processing component configured to determine the reflectance spectrum of the medium at the surface area at multiple wavelengths around an isosbestic wavelength of the first absorber and the second absorber;

a calculating component configured to determine a derivative of the determined reflectance spectrum around the isosbestic wavelength; and an estimating component configured to estimate a concentration ratio of the first concentration and the second concentration from the derivative.

In an embodiment of the apparatus, wherein the optical imaging device is a 2D hyperspectral optical imaging device comprising an image sensor having a plurality of pixels, the image processing component is further configured to:

assign a cluster of pixels to the surface area of the medium;

determine the reflectance spectrum for each pixel of the image sensor; and determine the reflectance spectrum of the medium at the surface area from the reflectance spectra of the pixels of the cluster.

In a fourth aspect of the invention, an apparatus for determining a property of an optically diffuse medium is provided. The medium comprises a first optical absorber having a first concentration and a second optical absorber having a second concentration. The apparatus comprises:

a light source configured to illuminate a surface area of a volume of the medium;

a spectrograph configured to receive reflected light from the surface area of the medium;

a light processing component configured to determine the reflectance spectrum of the medium at the surface area at multiple wavelengths around an isosbestic wavelength of the first absorber and the second absorber;

a calculating component configured to determine a derivative of the determined reflectance spectrum around the isosbestic wavelength; and an estimating component configured to estimate a concentration ratio of the first concentration and the second concentration from the derivative.

In a fifth aspect of the invention, a computer program of computer program product is provided. The computer program comprises computer instructions which, when loaded in a processor, enable the processor to carry out the method of the invention.

In a sixth aspect of the invention, a non-volatile storage medium is provided. The storage medium stores computer instructions which, when loaded in a processor, enable the processor to carry out the method of the invention.

Briefly stated, the present invention provides a method, apparatus and software for accurate diffuse optical imaging. The apparatus comprises a light source emitting a plurality of wavelengths and an optical imaging device capable of producing images at a number of prescribed wavelength bands. Images taken at strategically chosen wavelength bands may be combined to produce an image representing a twodimensional spatial distribution of the ratio of two absorbing substances.

It is noted that in diffuse reflection the light incident on the surface has entered the medium and has travelled through the medium, sometimes more than a cm, before being emitted again from the same surface.

In the case of specular reflection, a part of the incident light is directly reflected from the surface of the medium. It is desired to reduce such specular reflection, which is an additional benefit of the derivative algorithm outlined above.

In the case of specular reflection, expression 1.1 above becomes:

$$R_d = e^{-\mu_a(l)} + R_s \qquad (2.1)$$

where $R_s$ stands for the specular reflection. The specular reflection depends on the differences in refractive indices of the medium and of air and is expressed by Fresnel's equations. For normal incidence the specular reflectance $R_s$ is given by:

$$R_s = \left(\frac{n_{medium} - 1}{n_{medium} + 1}\right)^2 \qquad (2.2)$$

The specular reflection can be substantial, e.g. for a refractive index of tissue of 1.35 the specular reflection is more than 2%. For oblique incidence this can be even higher. In general this can be more than the diffuse reflection. The specular reflection does not contain information about the composition of the tissue and is considered a disturbing factor in many situations. Derivative imaging offers a solution here.

The effect of specular reflection is shown by entering the specular reflection into expression (1.11):

$$DX = \frac{\ln((R_s(\lambda_0 + \Delta\lambda) + R_d(\lambda_0 + \Delta\lambda))) - \ln((R_s(\lambda_0 + \Delta\lambda) + R_d(\lambda_0 - \Delta\lambda)))}{2\ln((R_s(\lambda_0 + \Delta\lambda) + R_d(\lambda_0)))} \qquad (2.3)$$

The analysis as described above leading to a fat-to-water ratio should be adapted: the contribution of $R_c$ is large and cannot be neglected.

Hence, a slightly different approach is followed. The derivative is still used, but there is no normalization with respect to the reflection:

$$UDX = R_s(\lambda_0 + \Delta\lambda) + R_d(\lambda_0 + \Delta\lambda) - (R_s(\lambda_0 + \Delta\lambda) + R_d(\lambda_0 - \Delta\lambda)) \qquad (2.4)$$

where UDX is an non-normalized imaging ratio.

For media such as human tissue, the refractive index varies only a few percent over a large wavelength region. For instance for human colon, the refractive index decreases from 1.37 at 500 nm to 1.32 at 1550 nm[1]. In the Near Infrared the specular reflectance $R_s$ (expression (2.2)) changes only $10^{-6}$ per nanometre. As a consequence expression (2.4) changes into:

$$UDX = R_d(\lambda_0 + \Delta\lambda) - R_d(\lambda_0 - \Delta\lambda) \qquad (2.5)$$

[1] Complex refractive index of normal and malignant human colorectal tissue in the visible and near-infrared. Giannios P, Koutsoumpos S, Toutouzas K G, Matiatou M, Zografos G C, Moutzouris K. J Biophotonics. 2016 Apr. 19. doi: 10.1002/jbio.201600001

A linear expansion around $\lambda_0$ yields:

$$UDX = 2\Delta\lambda \frac{dR_d}{d\lambda} \qquad (2.6)$$

Using expression (1.1), it can be derived:

$$UDX = -2\Delta\lambda R_d(\lambda_0) \frac{d\mu_a(\lambda)}{d\lambda} \qquad (2.7)$$

Replacing $R_d(\lambda_0)$ by $R_0$ and introducing the concentration ratio $\psi$ from expression (1.5) yields:

$$UDX = -2\Delta\lambda \frac{R_o}{\mu_{a,0}} \left( \psi \frac{\partial \mu_{a,1}}{\partial \lambda} \bigg|_{\lambda_0} + (1-\psi) \frac{\partial \mu_{a,2}}{\partial \lambda} \bigg|_{\lambda_0} \right) \qquad (2.8)$$

The concentration ratio $\psi$ can now be calculated from:

$$\psi = UDX \frac{1}{2\Delta\lambda} \frac{\mu_{a,0}}{R_o} \frac{\frac{\partial \mu_{a,2}}{\partial \lambda}\big|_{\lambda_0}}{\frac{\partial \mu_{a,1}}{\partial \lambda}\big|_{\lambda_0} - \frac{\partial \mu_{a,2}}{\partial \lambda}\big|_{\lambda_0}} \qquad (2.9)$$

In other words, by imaging UDX as defined in expression (2.4), a quantity is imaged that is proportional to the concentration ratio of the two chromophores that have an isosbestic point at $\lambda_0$. A difference with the method above is that the proportionality constant is not known a priori, but the image is completely free of specular reflections. A similar outcome applies for second and higher derivatives.

These and other aspects of the invention will be more readily appreciated as the same becomes better understood by reference to the following detailed description and considered in connection with the accompanying drawings in which like reference symbols designate like parts.

BRIEF DESCRIPTION OF THE DRAWINGS

FIGS. 8a, 8b, 8c and 8d illustrate a specular reflection reduction using a non-normalized imaging ratio.

FIGS. 9a, 9b, 9c, 9d, 9e and 9f illustrate test results in distinguishing invasive ductal carcinoma, IDC.

FIGS. 10a, 10b, 10c, 10d, 10e and 10f illustrate test results in distinguishing invasive ductal carcinoma, IDC, and ductal carcinoma in situ, DCIS.

FIGS. 11a, 11b, 11c, 12a, 12b, 12c and 12d illustrate a phantom study with an optical phantom.

DETAILED DESCRIPTION OF THE INVENTION

Figure 1:
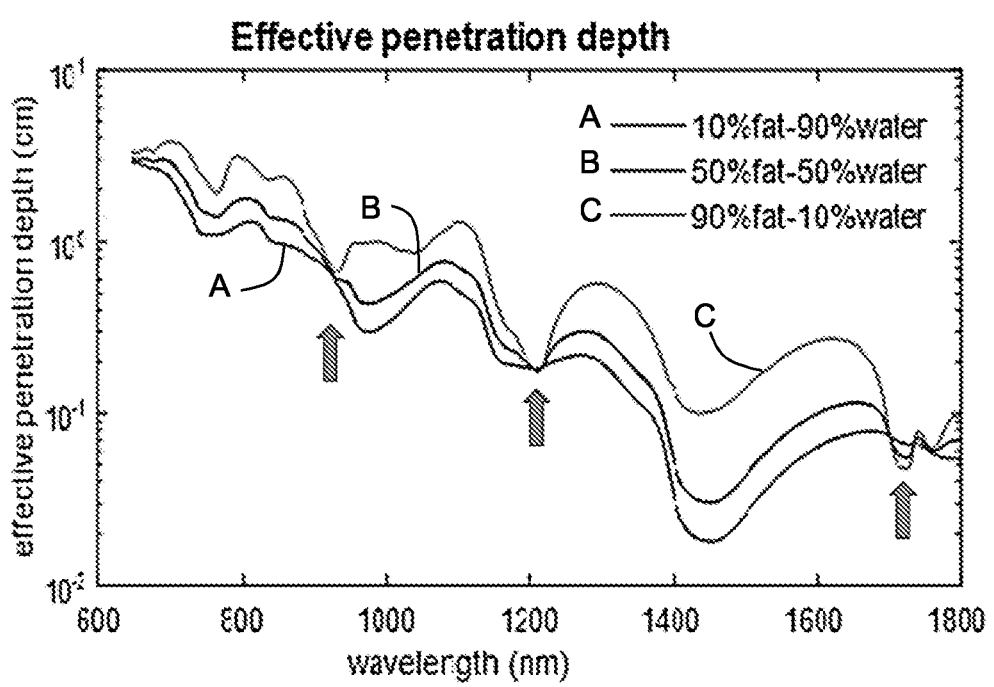
FIG. 1 depicts a diagram showing graphs of an effective penetration depth [cm] at different wavelengths [nm] of a medium containing different ratios of fat and water.

FIG. 1 depicts a diagram showing graphs of an effective penetration depth [cm] at different wavelengths [nm] of a medium containing different ratios of fat (a first optical absorber having a first concentration) and water (a second optical absorber having a second concentration). The optical penetration depths have been calculated with diffusion theory.

In a first (low) graph, marked A, the effective penetration depth versus wavelength for a medium containing 10% by volume of fat and 90% by volume of water is shown. In a second (middle) graph, marked B, the effective penetration depth versus wavelength for a medium containing 50% by volume of fat and 50% by volume of water is shown. In a third (high) graph, marked C, the effective penetration depth versus wavelength for a medium containing 90% by volume of fat and 10% by volume of water is shown.

As indicated in FIG. 1 by upwards pointing arrows, different isosbestic points (wavelengths) can be identified, at about 930 nm, about 1217 nm, about 1700 nm, and about 1736 nm, respectively. At these wavelengths, the effective (optical) penetration depth is the same for the different ratios of fat and water according to graphs A, B and C, and for other ratios of fat and water. Also, at these wavelengths, inhomogeneous distributions of fat and water in the medium do not influence the optical penetration depth.

In case the optical properties of the two absorbers, i.e. the first optical absorber fat and the second optical absorber water, do not differ much, a concentration ratio cannot be determined at an isosbestic wavelength.

Figure 2:
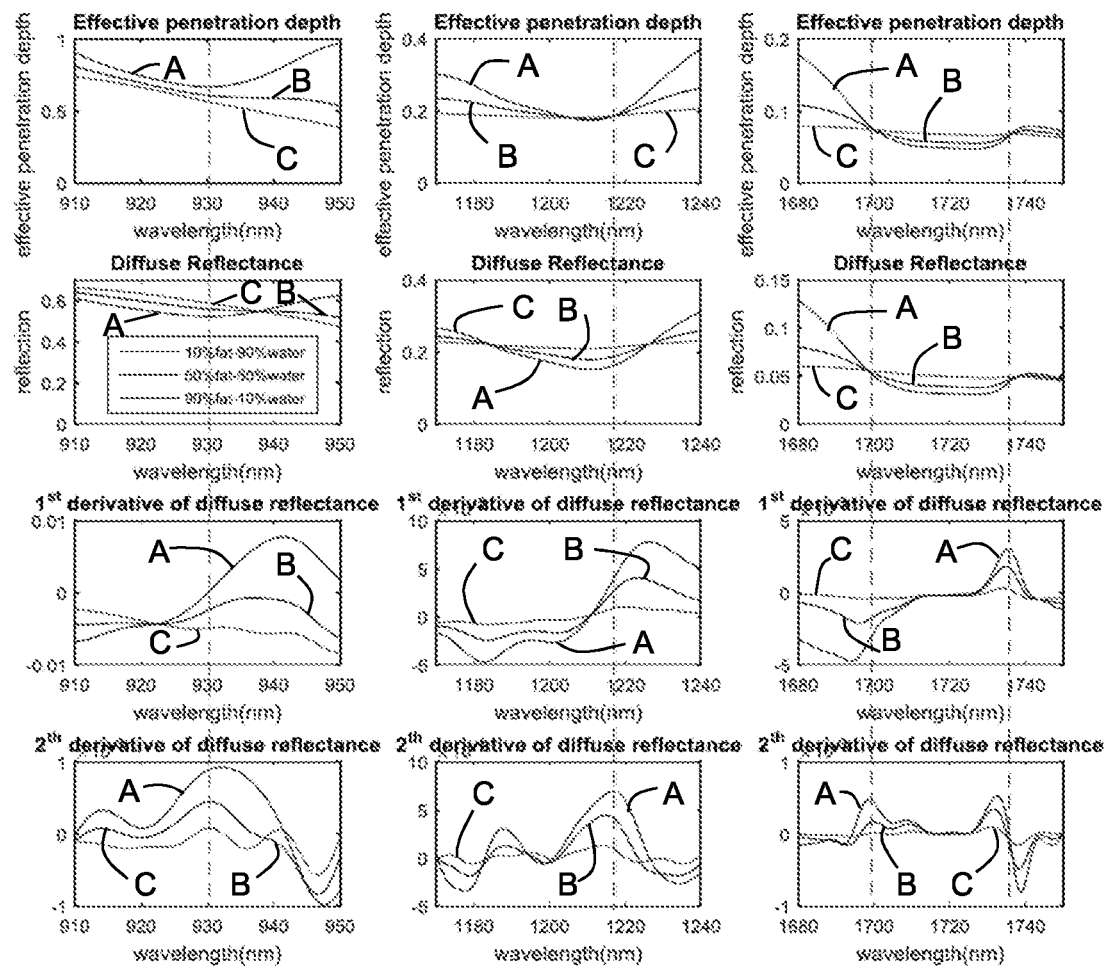
FIG. 2 depicts different diagrams showing graphs of effective penetration depth versus wavelength, diffuse reflectance versus wavelength, first derivative of diffuse reflectance versus wavelength, and second derivative of diffuse reflectance versus wavelength, all at three different wavelength ranges.

Hence, FIG. 2 depicts different diagrams showing graphs of effective penetration depth versus wavelength, diffuse reflectance versus wavelength, first derivative of diffuse reflectance versus wavelength, and second derivative of diffuse reflectance versus wavelength, all at three different wavelength ranges around isosbestic wavelengths.

In a left column comprising four diagrams, from top to bottom an effective penetration depth, an associated diffuse reflectance, and associated first derivative of the diffuse reflectance, and an associated second derivative of the diffuse reflectance, respectively, are shown for three different concentration ratios of fat and water (10/90 (graph A), 50/50 (graph B), and 90/10 (graph C)), in a first wavelength range from 910 nm to 950 nm around an isosbestic wavelength of about 930 nm, as indicated by a vertical dashed line.

In a middle column comprising four diagrams, from top to bottom an effective penetration depth, an associated diffuse reflectance, and associated first derivative of the diffuse reflectance, and an associated second derivative of the diffuse reflectance, respectively, are shown for three different concentration ratios of fat and water (10/90 (graph A), 50/50 (graph B), and 90/10 (graph C)), in a second wavelength range from 1170 nm to 1240 nm around an isosbestic wavelength of about 1217 nm, as indicated by a vertical dashed line.

In a right column comprising four diagrams, from top to bottom an effective penetration depth, an associated diffuse reflectance, and associated first derivative of the diffuse reflectance, and an associated second derivative of the diffuse reflectance, respectively, are shown for three different concentration ratios of fat and water (10/90 (graph A), 50/50 (graph B), and 90/10 (graph C)), in a third wavelength range from 1680 nm to 1750 nm around isosbestic wavelengths of about 1700 and 1736 nm, as indicated by vertical dashed lines.

From the third and fourth rows, each comprising three diagrams showing the first derivative and the second derivative, respectively, it can be seen these first and second derivatives of the diffuse reflection spectra clearly are different at the isosbestic wavelengths for different concentration ratios of the first optical absorber fat and the second optical absorber water.

Figure 3:
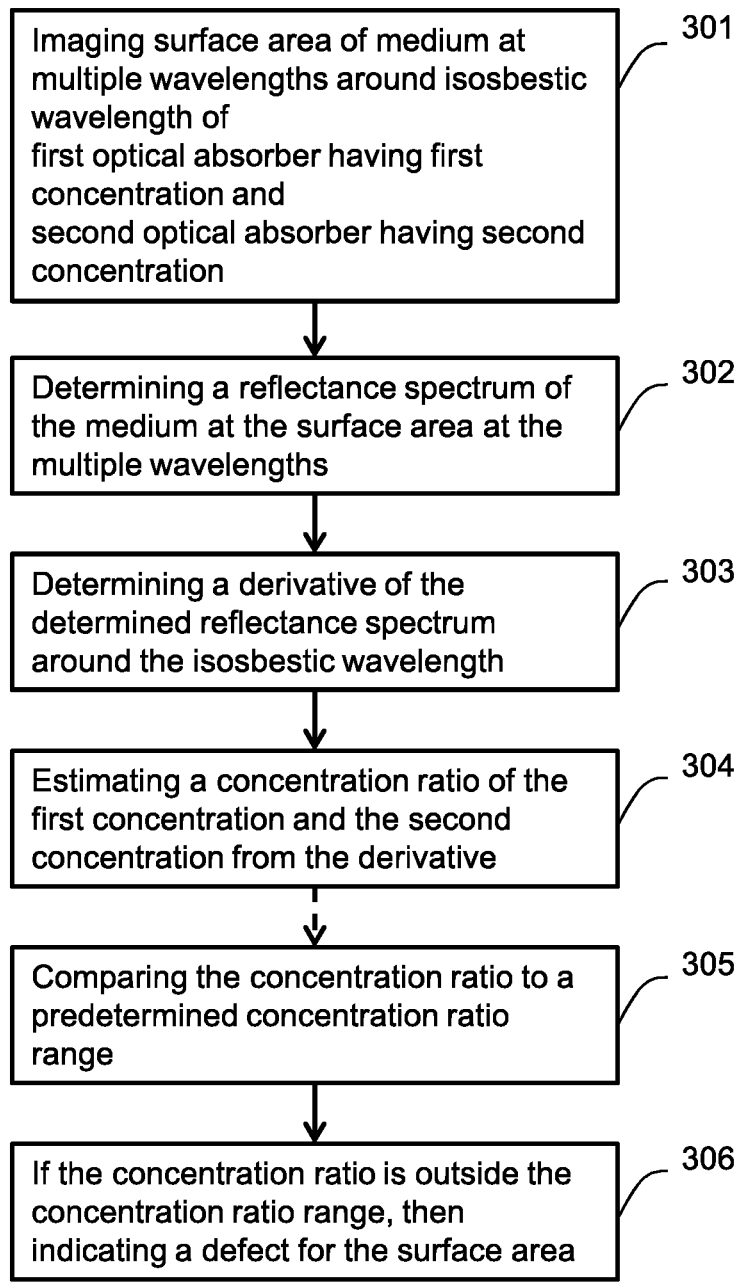
FIG. 3 depicts a flow diagram illustrating steps of an embodiment of a method according to the invention.

Based on this property of the diffuse reflection spectrum of a medium containing essentially two main optical absorbers, the following method is proposed, as illustrated in the flow diagram of FIG. 3.

With the method, a property of an optically diffuse medium, in particular a concentration ratio of a first concentration of a first optical absorber and a second concentration of a second optical absorber, can be determined, i.e. estimated.

In a step 301, a surface area of the medium is imaged at multiple wavelengths around an isosbestic wavelength of the first absorber and the second absorber. The surface area is selected to be in conformity with the spatial resolution to be expected for the medium. The imaging may be performed using an appropriate optical imaging device, as will be explained below by reference to FIGS. 4 to 7.

In FIG. 3, in a subsequent step 302, a reflectance spectrum of the medium is determined at the surface area at the multiple wavelengths.

In a subsequent step 303, a derivative of the determined reflectance spectrum around the isosbestic wavelength is determined.

In a subsequent step 304, a concentration ratio of the first concentration and the second concentration is estimated from the derivative. In particular, a concentration ratio $\psi$ may be determined using the following expression:

$$\psi = \frac{\frac{2DX}{\Delta\lambda} - \frac{\partial\mu_{a,2}}{\partial\lambda}\big|_{\lambda_0}}{\frac{\partial\mu_{a,1}}{\partial\lambda}\big|_{\lambda_0}} \cdot \frac{\mu_{a,0}}{\frac{\partial\mu_{a,2}}{\partial\lambda}\big|_{\lambda_0}} = \frac{\frac{2DX}{\Delta\lambda} - g}{f - g}$$

where:
f and g are defined by $$f = \frac{\frac{\partial\mu_{a,1}}{\partial\lambda}\big|_{\lambda_0}}{\mu_{a,0}} \text{ and } g = \frac{\frac{\partial\mu_{a,2}}{\partial\lambda}\big|_{\lambda_0}}{\mu_{a,0}};$$

$\lambda$ indicates a wavelength;
$\lambda_0$ indicates an isosbestic wavelength;
$\Delta\lambda$ indicates a wavelength difference from the isosbestic wavelength;
DX indicates an imaging ratio, defined by subtracting two images taken $\Delta\lambda$ apart from an isosbestic wavelength $\lambda_0$ and dividing by the sum of the two images;
$\mu_{a,m}$ indicates a molar absorption coefficient of absorber m;
$\mu_{a,0}$ indicates a molar absorption coefficient at isosbestic wavelength.

Once the concentration ratio $\psi$ has been determined, then according to step 305, it may be compared to a predetermined concentration ratio range. This predetermined concentration ratio range may have been established based on evidence that certain concentration ratios within the range are normal for the medium. Other concentration ratios outside the concentration ratio range are abnormal for the medium, and therefore may be qualified as a defect. According to step 306, if the concentration ratio is outside the concentration ratio range, a defect is indicated for the surface area of the medium, in an appropriate way.

The steps 302 to 306 may be performed by components of one or more (data) processing devices and associated input and output devices.

Figure 4:
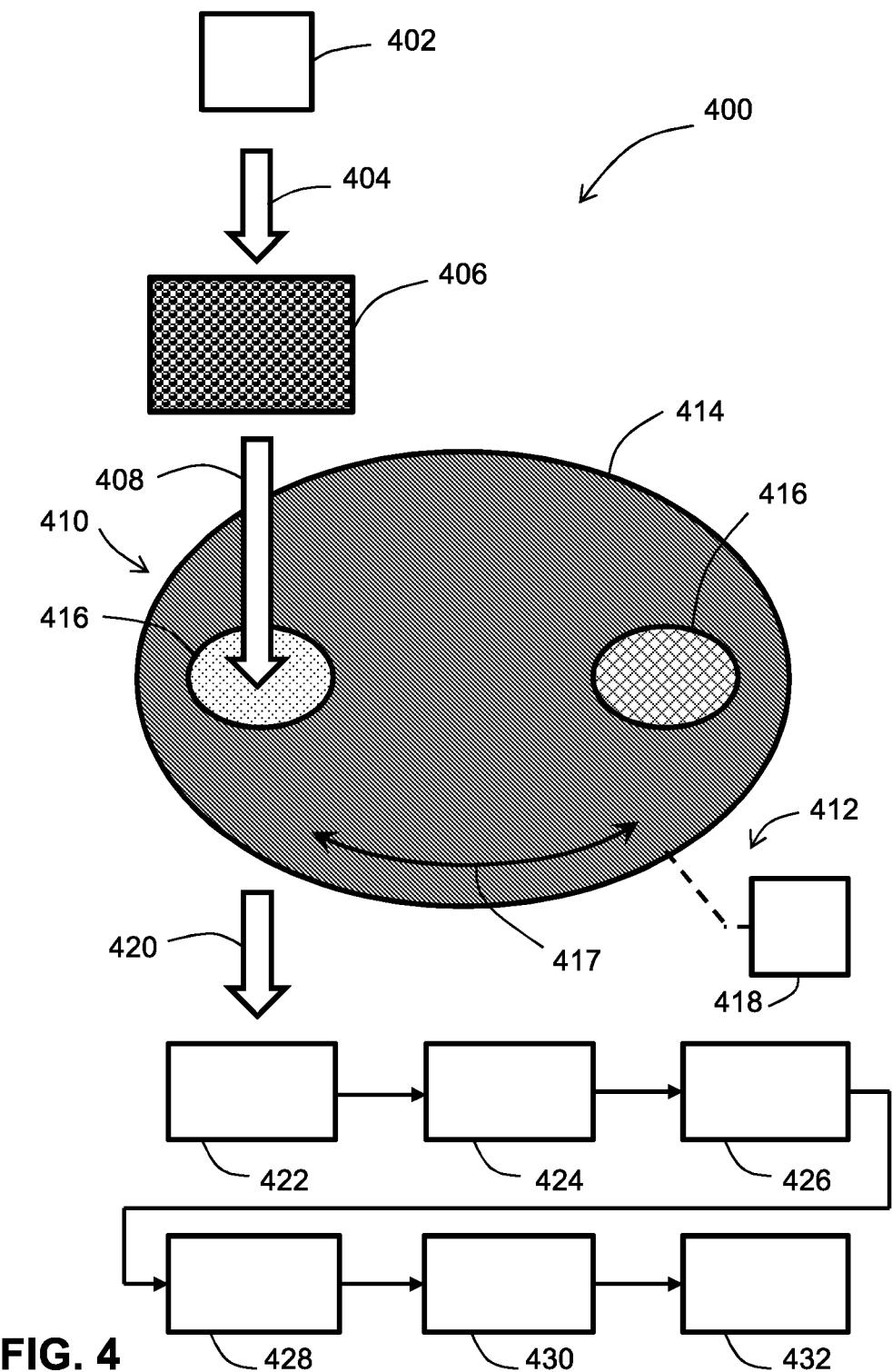
FIG. 4 schematically illustrates components of a first embodiment of an apparatus according to the invention.

FIG. 4 schematically illustrates components of a first embodiment of an apparatus 400 according to the invention.

The apparatus 400 comprises a light source 402 configured to illuminate (as indicated by arrow 404) a surface area 406 of a volume of an optically diffuse medium. The medium comprises a first optical absorber having a first concentration and a second optical absorber having a second concentration. Light is reflected (as indicated by arrow 408) from the surface area 406 of the medium to a filtering device 410 configured to receive such reflected light from the surface area of the medium, and to transmit filtered light (as indicated by arrow 420) to a twodimensional, 2D, optical imaging device 422 configured to receive the filtered light 420 from the filtering device 410.

The filtering device 410 is configured to filter multiple wavelengths around an isosbestic wavelength of the first absorber and the second absorber. The filtering device 410 comprises a mechanical device 412 (also referred to as a filter wheel) comprising a filter support 414 with multiple different optical filters 416 each filtering a different wavelength from the reflected light 408. In the mechanical device 412, the filter support 414 which can be rotated in either one of directions indicated by double arrow 417 by an actuator 418 coupled to the filter support 414, whereby each one of the multiple optical filters 416 can be positioned in the optical path of the reflected light 408 to provide light 420 filtered at different wavelengths.

The optical imaging device 422 may e.g. comprise a CCD camera, an InGaAs camera or a CMOS camera, and provides image data which are transferred to an image processing component 424 configured to determine a reflectance spectrum of the medium at the surface area 406 at the multiple wavelengths. Data relating to the reflectance spectrum are transferred from the image processing component 424 to a calculating component 426 configured to determine a derivative of the determined reflectance spectrum around the isosbestic wavelength. Data relating to the derivative of the determined reflectance spectrum around the isosbestic wavelength are transferred from the calculating component 426 to an estimating component 428 configured to estimate a concentration ratio $\psi$ of the first concentration and the second concentration from the derivative. Data relating to an estimated concentration ratio $\psi$ are transferred to a comparator 430 configured to compare the concentration ratio $\psi$ to a predetermined concentration ratio range. The comparator 430 controls an output component 432, such as an image output component, configured to indicate a defect for the surface area 406 when the concentration ratio $\psi$ is outside the concentration ratio range. For example, if a defect is to be indicated for the surface area 406, the output component 432 may display the surface area 406 having a color or any other indication to differentiate the surface area 406 from other surface areas for which a defect is not to be indicated.

Figure 5:
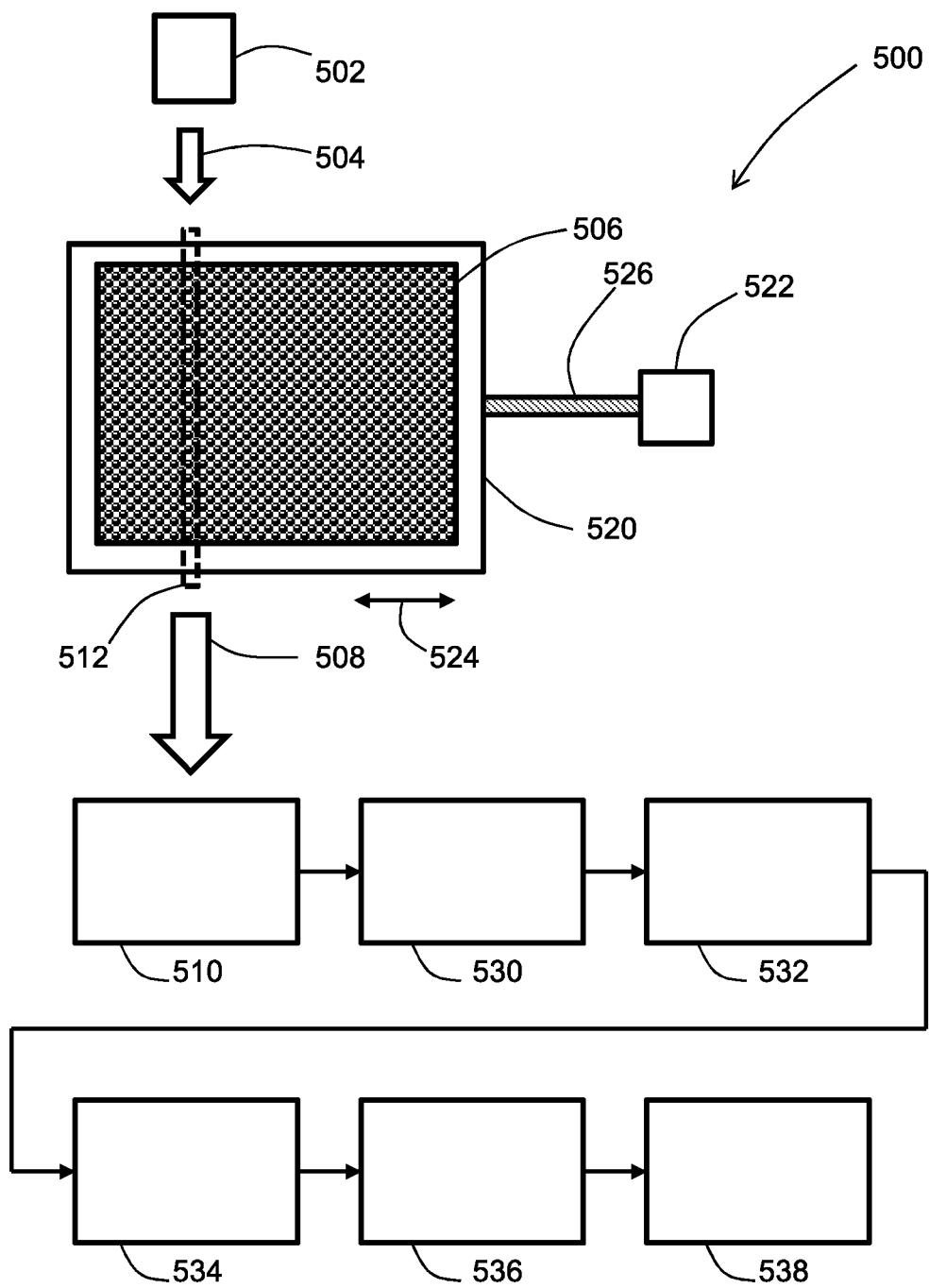
FIG. 5 schematically illustrates components of a second embodiment of an apparatus according to the invention.

FIG. 5 schematically illustrates components of a second embodiment of an apparatus 500 according to the invention.

The apparatus 500 comprises a light source 502 configured to illuminate (as indicated by arrow 504) a surface area 506 of a volume of an optically diffuse medium. The medium comprises a first optical absorber having a first concentration and a second optical absorber having a second concentration. Light is reflected (as indicated by arrow 508) from the surface area 506 of the medium. The apparatus 500 further comprises a onedimensional, 1D, hyperspectral optical imaging device 510 configured to receive reflected light 508 from a scanned line 512 of the surface area 506 of the medium. For each pixel of the hyperspectral optical imaging device 510, an entire spectrum is acquired.

The medium is supported on a stage 520 coupled to an actuator 522 configured to drive the stage 520 to move the medium relative to the optical imaging device 510 in directions as indicated by double arrow 524. For example, the actuator 522 is coupled to the stage 520 through a rotatable spindle 526 to move the stage 520. By incrementally moving the stage 520, different lines of the surface area 506 are imaged.

The 1D optical imaging device 510 comprises, for example, a CCD, InGaAs or CMOS hyperspectral camera, and acquires image data in the form of a $(x,y,\lambda)$ (x-coordinate, y-coordinate, wavelength) data cube, from which imaging wavelengths are chosen to select images. The optical imaging device 510 provides the selected image data which are transferred to an image processing component 530 configured to determine the reflectance spectrum of the medium at the surface area 506 at multiple wavelengths around an isosbestic wavelength of the first absorber and the second absorber. Data relating to the reflectance spectrum are transferred from the image processing component 530 to a calculating component 532 configured to determine a derivative of the determined reflectance spectrum around the isosbestic wavelength. Data relating to the derivative of the determined reflectance spectrum around the isosbestic wavelength are transferred from the calculating component 532 to an estimating component 534 configured to estimate a concentration ratio $\psi$ of the first concentration and the second concentration from the derivative. Data relating to an estimated concentration ratio $\psi$ are transferred to a comparator 536 configured to compare the concentration ratio $\psi$ to a predetermined concentration ratio range. The comparator 536 controls an output component 538, such as an image output component, configured to indicate a defect for the surface area 506 when the concentration ratio $\psi$ is outside the concentration ratio range. For example, if a defect is to be indicated for the surface area 506, the output component 538 may display the surface area 506 having a color or any other indication to differentiate the surface area 506 from other surface areas for which a defect is not to be indicated.

Figure 6:
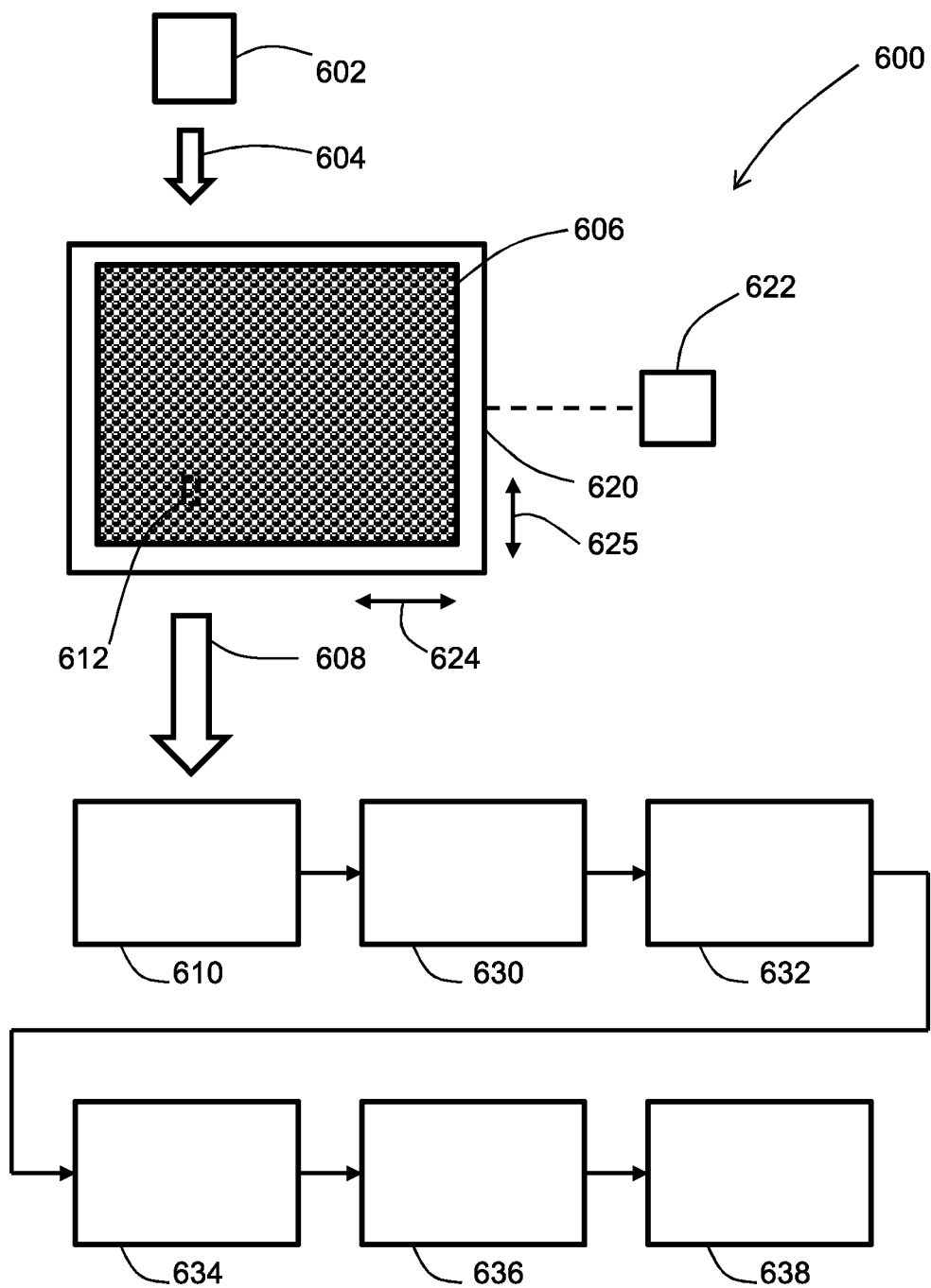
FIG. 6 schematically illustrates components of a third embodiment of an apparatus according to the invention.

FIG. 6 schematically illustrates components of a third embodiment of an apparatus 600 according to the invention.

The apparatus 600 comprises a light source 602 configured to illuminate (as indicated by arrow 604) a surface area 606 of a volume of an optically diffuse medium. The medium comprises a first optical absorber having a first concentration and a second optical absorber having a second concentration. Light is reflected (as indicated by arrow 608) from the surface area 606 of the medium. The apparatus 600 further comprises a twodimensional, 2D, hyperspectral optical imaging device 610 configured to receive reflected light 608 from a scanned surface sub-area 612 of the surface area 606 of the medium. For each pixel of the hyperspectral optical imaging device 610, an entire spectrum is acquired.

The medium is supported on a stage 620 coupled to an actuator 622 configured to drive the stage 620 to move the medium relative to the optical imaging device 610 in directions as indicated by double arrows 624, 625. By incrementally moving the stage 620, different surface sub-areas 612 of the surface area 606 are imaged.

In another embodiment lacking a stage, different surface sub-areas 612 of the surface area 606 may be scanned by use of movable scanning mirrors (not shown) directing the reflected light 608 to the 2D optical imaging device 610.

The 2D optical imaging device 610 comprises, for example, a CCD, InGaAs or CMOS hyperspectral camera, and acquires image data in the form of a (x,y,λ) (x-coordinate, y-coordinate, wavelength) data cube, from which imaging wavelengths are chosen to select images. The optical imaging device 610 provides the selected image data which are transferred to an image processing component 630 configured to determine the reflectance spectrum of the medium at the surface area 606 at multiple wavelengths around an isosbestic wavelength of the first absorber and the second absorber.

The 2D hyperspectral optical imaging device 610 comprises an image sensor having a plurality of pixels. The image processing component 630 is configured to assign a cluster of pixels of the image sensor to the surface sub-area 612 of the medium, to determine the reflectance spectrum for each pixel of the image sensor, and to determine the reflectance spectrum of the medium at the surface area 606 from the reflectance spectra of the pixels of the cluster.

Data relating to the reflectance spectrum are transferred from the image processing component 630 to a calculating component 632 configured to determine a derivative of the determined reflectance spectrum around the isosbestic wavelength. Data relating to the derivative of the determined reflectance spectrum around the isosbestic wavelength are transferred from the calculating component 632 to an estimating component 634 configured to estimate a concentration ratio ψ of the first concentration and the second concentration from the derivative. Data relating to an estimated concentration ratio ψ are transferred to a comparator 636 configured to compare the concentration ratio ψ to a predetermined concentration ratio range. The comparator 636 controls an output component 638, such as an image output component, configured to indicate a defect for the surface area 606 when the concentration ratio ψ is outside the concentration ratio range. For example, if a defect is to be indicated for the surface area 606, the output component 638 may display the surface area 606 having a color or any other indication to differentiate the surface area 606 from other surface areas for which a defect is not to be indicated.

It is noted that, instead of a 2D hyperspectral optical imaging device 610, a spectrograph can be applied, as explained by reference to FIG. 7.

Figure 7:
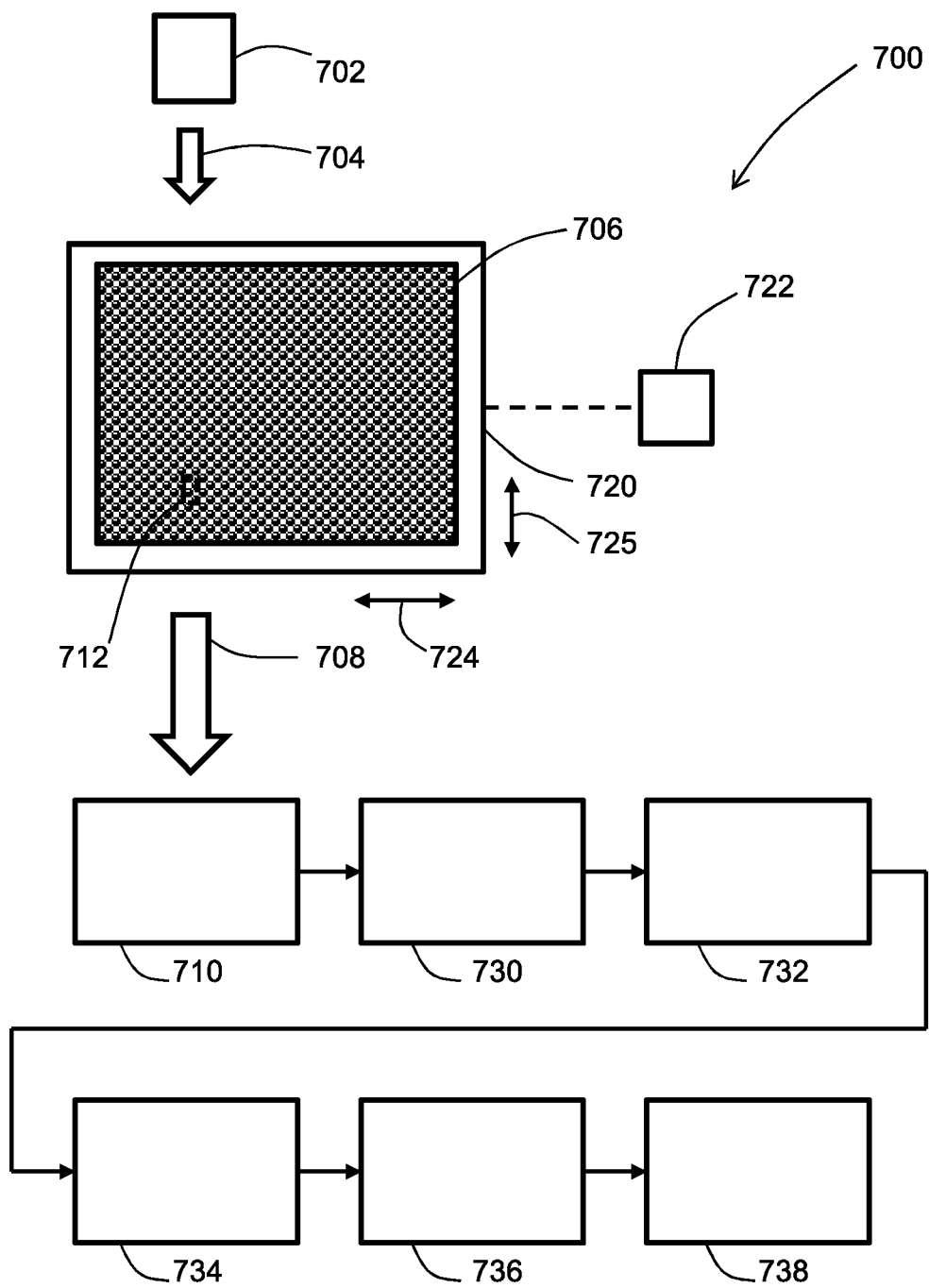
FIG. 7 schematically illustrates components of a fourth embodiment of an apparatus according to the invention.

FIG. 7 schematically illustrates components of a fourth embodiment of an apparatus 700 according to the invention.

The apparatus 700 comprises a light source 702 configured to illuminate (as indicated by arrow 704) a surface area 706 of a volume of an optically diffuse medium. The medium comprises a first optical absorber having a first concentration and a second optical absorber having a second concentration. Light is reflected (as indicated by arrow 708) from the surface area 706 of the medium. The apparatus 700 further comprises a spectrograph 710 configured to receive reflected light 708 from a scanned surface sub-area 712 of the surface area 706 of the medium. For each pixel of the spectrograph 710, an entire spectrum is acquired.

The medium is supported on a stage 720 coupled to an actuator 722 configured to drive the stage 720 to move the medium relative to spectrograph 710 in directions as indicated by double arrows 724, 725. By incrementally moving the stage 720, different surface sub-areas 712 of the surface area 706 are imaged.

In another embodiment lacking a stage, different surface sub-areas 712 of the surface area 706 may be scanned by use of a scanning device comprising movable scanning mirrors (not shown) directing the reflected light 708 to the spectrograph 710.

The spectrograph 710 acquires image data in the form of a (x,y,λ) (x-coordinate, y-coordinate, wavelength) data cube, from which imaging wavelengths are chosen to select images. The spectrograph 710 provides the selected image data which are transferred to an image processing component 730 configured to determine the reflectance spectrum of the medium at the surface area 706 at multiple wavelengths around an isosbestic wavelength of the first absorber and the second absorber.

Data relating to the reflectance spectrum are transferred from the image processing component 730 to a calculating component 732 configured to determine a derivative of the determined reflectance spectrum around the isosbestic wavelength. Data relating to the derivative of the determined reflectance spectrum around the isosbestic wavelength are transferred from the calculating component 732 to an estimating component 734 configured to estimate a concentration ratio ψ of the first concentration and the second concentration from the derivative. Data relating to an estimated concentration ratio ψ are transferred to a comparator 736 configured to compare the concentration ratio ψ to a predetermined concentration ratio range. The comparator 736 controls an output component 738, such as an image output component, configured to indicate a defect for the surface area 706 when the concentration ratio ψ is outside the concentration ratio range. For example, if a defect is to be indicated for the surface area 706, the output component 738 may display the surface area 706 having a color or any other indication to differentiate the surface area 706 from other surface areas for which a defect is not to be indicated.

Test Results

Diffuse Reflection

FIG. 8a shows a number of spectra taken from different locations in a sample, indicating on a horizontal axis a wavelength in nm in steps of 100 nm from about 900 nm to about 1700 nm, and indicating on a vertical axis a diffuse reflectance (unscaled). Curves 801 and 802 show a spectrum from pixels of the sample with specular reflection, whereas the other curves show spectra from other areas. In a comparison of curve 803 with curve 801, and comparing curve 804 with curve 802, FIG. 8a illustrates that the spectra affected by specular reflection do not change shape, but are only shifted, as a wavelength independent amount of reflection is added by the specular reflection to the diffuse reflection from the tissue.

FIGS. 8b, 8c and 8d illustrate that the first and second derivative can be helpful in decreasing the effects of specular reflection.

FIG. 8b shows a spectral image of a breast tissue sample at 940 nm. This sample had a very irregular surface causing multiple specular reflections, recognised by the bright white areas 810 in the image.

FIG. 8c shows a first derivative image around 1225 nm. A much smoother image with normal derivative values even in many of the pixels that were originally affected by specular reflection results. The dark areas as indicated by arrows 805 indicate pixels where one of the pixel values used to calculate the first derivative had reached a saturation level. In such a case the first derivative algorithm cannot compensate the specular reflection.

FIG. 8d shows a second derivative image around 1225 nm. The image is noisier, but still a smooth image where only a few pixels remain affected by specular reflection, as indicated by arrow 805.

Distinguishing Invasive Ductal Carcinoma from Normal Tissue

FIGS. 9a, 9b, 9c, 9d, 9e and 9f illustrate test results in distinguishing invasive ductual carcinoma, IDC, confirming the excellent classification based on the first derivative. A collected dataset consists of samples of eight different patients. All these samples contained both IDC and healthy tissue. Hyperspectral data cubes were obtained from all samples and first derivative images around 1225 nm were calculated. In all images, regions of interest, ROI, were selected that, based on the histopathology, only contained IDC or healthy tissue. From these ROIs the first derivative values were calculated. A training set of 70% (randomly assigned) of these first derivative values was used to train a simple classification algorithm. An evaluation of the method was performed on the remaining 30% of the data.

FIG. 9a shows a regular grey shade picture of a tissue slice of a patient sample that was assigned to the test dataset. The sample consisted of fatty tissue and a large centrally located invasive ductal carcinoma, IDC. The specimen was obtained fresh from surgery and sliced by the pathologist.

FIG. 9b shows a hematoxylin-eosin, HE, stained section of the slice of FIG. 9a. Line 901 encircles the area indicated by the pathologist as IDC.

FIG. 9c shows the first derivative image of the slice taken around 1225 nm.

FIG. 9d shows a tissue classification on the basis of the first derivative using a cut-off value of 0.044. The central dark grey area 902 indicates IDC, the surrounding light grey area is normal tissue and the further dark area is background, i.e. an area where there was no sample. FIG. 9d clearly shows that the first derivative at 1225 nm can be used to distinguish IDC from normal tissue.

FIG. 9e shows a histogram of first derivative values from the test set, and clearly shows that the first derivative at 1225 nm markedly differentiates IDC from healthy tissue according to the pathologic classification, as indicated by arrows indicating the values for the different tissues. A horizontal axis indicates a value from the first derivative around 1225 nm in steps of 0.02 running from 0 to 0.16, and a vertical axis indicates a number of spectra with that value in steps of 10 running from 0 to 80. The dotted line represents the cut-off value of 0.0438, derived from the training set.

FIG. 9f shows a ROC curve indicating, on a horizontal axis, a false positive rate (1-Specificity) in steps of 0.2 running from 0 to 1, and on a vertical axis, a true positive rate (Sensitivity) in steps of 0.1 running from 0 to 1. Area under the curve, AUC, is 0.987 (confidence interval: 0.979-0.995).

Distinguishing Invasive Ductal Carcinoma and Ductal Carcinoma In Situ from Normal Tissue FIGS. 10a, 10b, 10c, 10d, 10e and 10f illustrate test results in distinguishing invasive ductal carcinoma, IDC, and ductal carcinoma in situ, DCIS. The collected dataset consist of samples of ten different patients. All these samples contained healthy tissue, eight out of ten samples contained IDC and six out of ten samples contained DCIS. DCIS is a form of cancer that is in an earlier stage and is sometime present as small volumes of cancer cells. It is generally agreed that often positive resection margin are related to small pockets of DCIS that much more difficult to see by the surgeon than larger tumours.

In these samples, regions of interest, ROI, were selected that, based on the histopathology, only contained IDC, DCIS or healthy tissue. The spectra in these ROIs were used as a training (~70% of the spectra) and test set (~30% of the spectra) for the first derivative algorithm. Of each patient, the spectra in the ROIs were randomly assigned to either the training set or the test set.

Referring to FIG. 10a, a regular grey shade picture of a patient sample is shown that was assigned to the test dataset. This sample, a tissue slice, exposes a large area of tumor tissue, and consists of fatty tissue, IDC and DCIS. The specimen was obtained fresh from surgery and coloured (according to standard pathology protocol) and sliced by the pathologist.

FIG. 10b shows a hematoxylin-eosin, HE, stained section of the slice of FIG. 10a. A line 1001 encircles the area indicated by the pathologist as IDC and DCIS.

FIG. 10c shows the first derivative image of the slice taken at 1225 nm.

FIG. 10d shows a tissue classification based on the first derivative using a cut-off value of 0.0486. The slice is indicated by a light grey area 1003. The central grey area 1002 indicates cancer, including both IDC and DCIS. Black areas appear in the sample where there were holes in the sample, or the sample thickness was too thin. As can be seen in FIGS. 10c and 10d, the large parts of IDC and DCIS were easily classified as tumor tissue. However, smaller DCIS branches were not detected. The width of these DCIS branches was less than 0.5 mm and since the path length of light is higher (2-2.5 mm), these small branches are missed. i.e. light acquired at this location has sampled a volume exceeding the DCIS branches and has picked up information from the surrounding fatty tissue making it look like fatty tissue.

FIG. 10e shows a histogram of first derivative values from the test set, and clearly shows that the first derivative at 1225 nm markedly differentiates both IDC and DCIS from healthy tissue, as indicated by arrows indicating the values for the different tissues. A horizontal axis indicates a value from the first derivative around 1225 nm in steps of 0.02 running from 0 to 0.14, and a vertical axis indicates a number of spectra with that value in steps of 10 running from 0 to 80. The dashed line indicates the position of a cut-off point of 0.0486.

FIG. 10f shows a ROC curve calculated with both IDC and DCIS spectra labelled as tumor and healthy spectra labelled as healthy tissue. FIG. 10f indicates, on a horizontal axis, a false positive rate (1-Specificity) in steps of 0.2 running from 0 to 1, and on a vertical axis, a true positive rate (Sensitivity) in steps of 0.1 running from 0 to 1. Area under the curve, AUC, is 0.998 (confidence interval: 0.982-0.995).

Phantom Study

FIGS. 11a, 11b, 11c, 12a, 12b, 12c and 12d illustrate test results in a phantom study using an optical phantom made out of pure coconut oil with embedded drops of Intralipid of different sizes. The coconut oil has a high fat content (close to 100%), Intralipid has a much lower fat content of 20%. This simulates a diffuse medium with inclusions of different sizes.

Figure 11A:
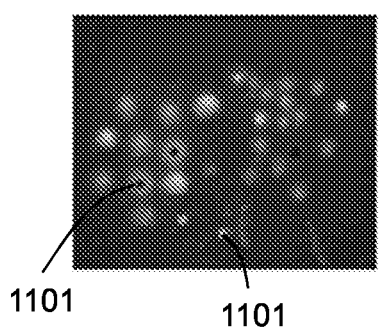

FIG. 11a shows a diffuse reflection image of the optical phantom taken at 1210 nm. It clearly shows Intralipid drops of various dimensions.

Figure 11B:
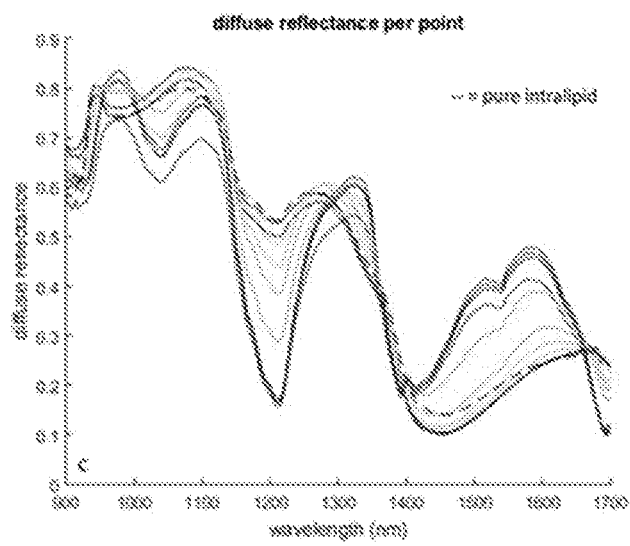

FIG. 11b shows the full spectra of locations 1101 marked with a dot in FIG. 11a, together with a spectrum taken from pure Intralipid shown as a dashed line. A horizontal axis indicates a wavelength [nm] in steps of 100 nm running from 900 to 1700 nm. A vertical axis indicates a diffuse reflectance in steps of 0.1 running from 0 to 0.9. As has been recognized, spectra taken on larger Intralipid drops are more similar to the spectrum of pure Intralipid, while the spectra taken on smaller Intralipid drops are more similar to the spectra taken from pure coconut oil (displaying the largest dip at 1210 nm). Spectra taken on smaller intralipid drops indicate a mixture between Intralipid and coconut oil.

FIGS. 11a and 11b clearly show the effect of the sampling depth. The size of the larger Intralipid drops was taken to be larger than the sampling depth at 1210 nm. Hence the spectra taken at the centre of these spots closely resemble the spectra of pure Intralipid. The spectra taken from the centres of the smaller drops contain information from both the Intralipid drop and their coconut oil environment and hence shows a mixture between the two spectra.

Figure 11C:
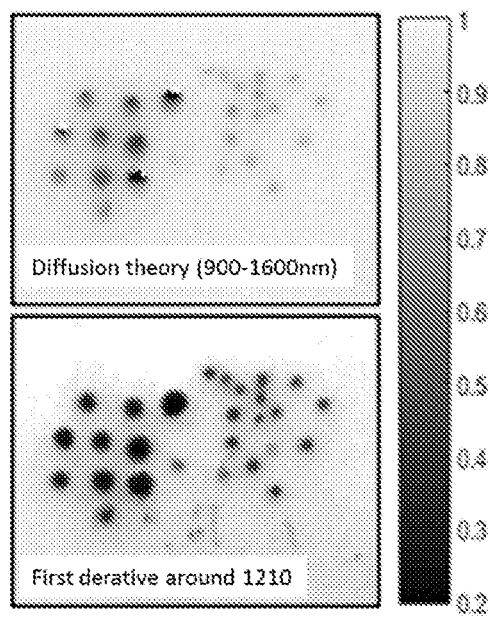

FIG. 11c illustrates fat-to-water ratios calculated from the hyperspectral data in two different ways. In the top image, a diffusion model was fitted containing the known absorption spectra of water and fat. In the bottom image, the first derivative image around 1210 nm was calculated. FIG. 11c clearly shows the effect of the wavelengths with large penetration depths on the fit of the diffusion model. The Intralipid droplets in the top image show a lower contrast for the smaller droplets.

FIGS. 12b and 12d show, for the optical phantom, fat-to-water ratios 1201, 1202 calculated with diffusion theory and the associated first deratives 1203, 1204, respectively, calculated along the trajectories indicated in white lines in FIGS. 12a and 12c. The trajectories were chosen such that they cross several small Intralipid droplets. In general, the apparent fat content of the Intralipid droplets is much higher when estimated through the fit of the diffusion model. It can be clearly seen that diffusion theory overestimates the fat to water ratio in these small inclusions.

FIGS. 12a, 12b, 12c and 12d clearly illustrate the effect that the large sampling volume used when applying diffusion theory in a wide wavelength range dilutes the signal from the volume of the Intralipid droplet with a signal from the surrounding coconut oil.

Products, such as software or apparatus, for imaging relative concentrations of light absorbing components/absorbers in (samples of) optically diffuse materials, e.g. find applications in the following fields.

Healthcare:
Diagnosis of disease by in vivo imaging of tissue components in suspect areas.
Assessment of resection margins by ex vivo imaging the ratio between fat and water concentrations in resection margins in the resection specimen.
Assessment of resection margins in vivo during surgery imaging the ratio between fat and water concentrations.
Evaluation of stool samples for colon cancer risk stratification.
Agro/Food:
Estimating freshness of fruit, meat or fish by quantitative imaging of essential components.
Estimating nutritional value of food by quantitative imaging of nutritional components.
Estimating a vase life of flowers.
Environmental:
Quality determination and monitoring of surface water.
Forensic:
Child abuse: Determination of the age of a bruise by accurate imaging of the spatial distribution of biochemical components occurring in haemoglobin breakdown.
Crime scene evaluation: determination of the age of blood stains or other traces of other bodily fluids.
Forensic pathology: Determination of the time of death by accurate imaging of the distribution of biochemical components occurring in livor mortis.

As explained in detail above, in a method and apparatus, a property of an optically diffuse medium comprising a first optical absorber having a first concentration and a second optical absorber having a second concentration is determined. A surface area of the medium is imaged at multiple wavelengths around an isosbestic wavelength of the first absorber and the second absorber. A reflectance spectrum of the medium at the surface area at the multiple wavelengths is determined. A derivative of the determined reflectance spectrum around the isosbestic wavelength is determined. From the derivative, a concentration ratio of the first concentration and the second concentration is estimated.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a"/"an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The term coupled, as used herein, is defined as connected, although not necessarily directly, and not necessarily mechanically.

A single processor or other unit may fulfil the functions of several items recited in the claims.

The terms software, program, software application, and the like as used herein, are defined as a sequence of instructions designed for execution in a processor of a computer system.

A program, computer program, or software application may include a subroutine, a function, a procedure, an object method, an object implementation, an executable application, an applet, a servlet, a source code, an object code, a shared library/dynamic load library and/or other sequence of instructions designed for execution on a computer system.

A computer program may be stored and/or distributed on a suitable non-volatile medium, such as an optical storage medium or a solid-state medium supplied together with or as part of other hardware, but also be distributed in other forms, such as via the Internet or other wired or wireless telecommunication systems.

The invention claimed is:

1. An apparatus for determining a property of an optically diffuse medium, the medium comprising a first optical absorber having a first concentration and a second optical absorber having a second concentration, the apparatus comprising:
a light source configured to illuminate a surface area of a volume of the medium;

a filtering device configured to receive reflected light from the surface area of the medium and to transmit filtered light to an optical imaging device, wherein the filtering device is configured to filter multiple wavelengths around an isosbestic wavelength of the first absorber and the second absorber;

a two-dimensional, 2D, optical imaging device configured to receive the filtered light from the filtering device;

an image processing component of a data processing device having a processor to load computer instructions enabling the processor to determine a reflectance spectrum of the medium at the surface area at the multiple wavelengths;

a calculating component of a data processing device having the processor to load computer instructions enabling the processor to determine a derivative of the determined reflectance spectrum around the isosbestic wavelength; and an estimating component of a data processing device having the processor to load computer instructions enabling the processor to estimate a concentration ratio ($\psi$) of the first concentration and the second concentration from the derivative of the determined reflectance spectrum around the isosbestic wavelength, wherein the concentration ratio ($\psi$) is determined using the partial derivative of a first molar absorption coefficient of the first absorber as a function of the wavelength, and the partial derivative of a second molar absorption coefficient of the second absorber as a function of the wavelength, both taken at a wavelength at which the first molar absorption coefficient and the second molar absorption coefficient are equal.

2. The apparatus according to claim 1, further comprising:
a comparator of the data processing device having the processor to load computer instructions enabling the processor to compare the concentration ratio ($\psi$) to a predetermined concentration ratio range; and an output component of the data processing device having the processor to load computer instructions enabling the processor to indicate a defect for the surface area when the concentration ratio is outside the concentration ratio range.

3. The apparatus according to claim 1, wherein the filtering device comprises:
a filter support comprising a plurality of different optical filters; and
an actuator to position each one of the optical filters in an optical path from the surface area of the medium to the optical imaging device.

4. The apparatus according to claim 1, wherein the optical imaging device comprises a CCD camera, an InGaAs camera or a CMOS camera.

5. A non-transitory storage medium storing computer instructions which, when loaded in the processor of the data processing device of claim 1 to carry out the steps of the image processing component, the calculating component and the estimating component.

6. The apparatus according to claim 1, wherein the concentration ratio ($\psi$) is determined as:

$$\psi = \frac{\frac{2DX}{\Delta\lambda} - \frac{\partial \mu_{a,2}}{\partial \lambda}\big|_{\lambda_0}}{\frac{\partial \mu_{a,1}}{\partial \lambda}\big|_{\lambda_0} - \frac{\partial \mu_{a,2}}{\partial \lambda}\big|_{\lambda_0}} = \frac{\frac{2DX}{\Delta\lambda} - g}{f - g}$$

where:
f and g are defined by $$f = \frac{\frac{\partial \mu_{a,1}}{\partial \lambda}\big|_{\lambda_0}}{\mu_{a,0}} \text{ and } g = \frac{\frac{\partial \mu_{a,2}}{\partial \lambda}\big|_{\lambda_0}}{\mu_{a,0}};$$

$\lambda$ indicates a wavelength;

$\lambda_0$ indicates an isosbestic wavelength;

$\Delta\lambda$ indicates a wavelength difference from the isosbestic wavelength;

DX indicates an imaging ratio, defined by subtracting two images taken $\Delta\lambda$ apart from an isosbestic wavelength $\lambda_0$ and dividing by the sum of the two images;

$\mu_{a,m}$ indicates a molar absorption coefficient of absorber m; and $\mu_{a,0}$ indicates a molar absorption coefficient at isosbestic wavelength.

7. The apparatus according to claim 1, wherein the derivative of the determined reflectance spectrum around the isosbestic wavelength is a first derivative.

8. The apparatus according to claim 1, wherein the estimating component of the data processing device further has the processor to load computer instructions enabling the processor to estimate a concentration ratio of the first concentration and the second concentration from the derivative of the determined reflectance spectrum around different isosbestic wavelengths of the first absorber and the second absorber in different wavelength regions to obtain estimated concentration ratios for each one of the isosbestic wavelengths.

9. The apparatus according to claim 8, further comprising:
a comparator of the data processing device having the processor to load computer instructions enabling the processor to compare each one of the estimated concentration ratios to a predetermined concentration ratio range; and an output component of the data processing device having the processor to load computer instructions enabling the processor to indicate a defect for the surface area when at least one of the concentration ratios is outside the concentration ratio range.

10. The apparatus according to claim 8, wherein the estimating component of the data processing device further has the processor to load computer instructions enabling the processor to associate each isosbestic wavelength with a respective optical penetration depth; and the apparatus further comprising an output component of the data processing device having the processor to load computer instructions enabling the processor to indicate a defect and a depth thereof for the surface area when at least one of the concentration ratios is outside the concentration ratio range.

11. The apparatus according to claim 8, wherein the estimating component of the data processing device further has the processor to load computer instructions enabling the processor to associate each isosbestic wavelength with a respective optical penetration depth and, if small defects are to be located, to select an isosbestic wavelength among different isosbestic wavelengths with a low optical penetration depth.

12. An apparatus for determining a property of an optically diffuse medium, the medium comprising a first optical absorber having a first concentration and a second optical absorber having a second concentration, the apparatus comprising:

a light source configured to illuminate a surface area of a volume of the medium;

a one-dimensional, 1D, or two-dimensional, 2D, hyperspectral optical imaging device configured to receive reflected light from the surface area of the medium;

an image processing component of a data processing device having a processor to load computer instructions enabling the processor to determine the reflectance spectrum of the medium at the surface area at multiple wavelengths around an isosbestic wavelength of the first absorber and the second absorber;

a calculating component of the data processing device having the processor to load computer instructions enabling the processor to determine a derivative of the determined reflectance spectrum around the isosbestic wavelength; and an estimating component of the data processing device having the processor to load computer instructions enabling the processor to estimate a concentration ratio ($\psi$) of the first concentration and the second concentration from the derivative of the determined reflectance spectrum around the isosbestic wavelength, wherein the concentration ratio ($\psi$) is determined using the partial derivative of a first molar absorption coefficient of the first absorber as a function of the wavelength, and the partial derivative of a second molar absorption coefficient of the second absorber as a function of the wavelength, both taken at a wavelength at which the first molar absorption coefficient and the second molar absorption coefficient are equal.

13. The apparatus according to claim 12, further comprising:

a stage configured to support the medium; and an actuator configured to drive the stage to move the medium relative to the optical imaging device.

14. The apparatus according to claim 12, wherein the optical imaging device is a 2D hyperspectral optical imaging device comprising an image sensor having a plurality of pixels, and wherein the image processing component is further configured to:

assign a cluster of pixels to the surface area of the medium;

determine the reflectance spectrum for each pixel of the image sensor; and determine the reflectance spectrum of the medium at the surface area from the reflectance spectra of the pixels of the cluster.

15. The apparatus according to claim 12, wherein the concentration ratio ($\psi$) is determined as:

$$\psi = \frac{\frac{2DX}{\Delta\lambda} - \frac{\frac{\partial \mu_{a,2}}{\partial \lambda}\big|_{\lambda_0}}{\mu_{a,0}}}{\frac{\frac{\partial \mu_{a,1}}{\partial \lambda}\big|_{\lambda_0}}{\mu_{a,0}} - \frac{\frac{\partial \mu_{a,2}}{\partial \lambda}\big|_{\lambda_0}}{\mu_{a,0}}} = \frac{\frac{2DX}{\Delta\lambda} - g}{f - g}$$

where:

f and g are defined by $$f = \frac{\frac{\partial \mu_{a,1}}{\partial \lambda}\big|_{\lambda_0}}{\mu_{a,0}} \text{ and } g = \frac{\frac{\partial \mu_{a,2}}{\partial \lambda}\big|_{\lambda_0}}{\mu_{a,0}};$$

$\lambda$ indicates a wavelength;

$\lambda_0$ indicates an isosbestic wavelength;

$\Delta\lambda$ indicates a wavelength difference from the isosbestic wavelength;

DX indicates an imaging ratio, defined by subtracting two images taken $\Delta\lambda$ apart from an isosbestic wavelength $\lambda_0$ and dividing by the sum of the two images;

$\mu_{a,m}$ indicates a molar absorption coefficient of absorber m; and $\mu_{a,0}$ indicates a molar absorption coefficient at isosbestic wavelength.

16. The apparatus according to claim 12, wherein the derivative of the determined reflectance spectrum around the isosbestic wavelength is a first derivative.

17. The apparatus according to claim 12, further comprising:

a comparator of the data processing device having the processor to load computer instructions enabling the processor to compare the concentration ratio ($\psi$) to a predetermined concentration ratio range; and an output component of the data processing device having the processor to load computer instructions enabling the processor to indicate a defect for the surface area when the concentration ratio is outside the concentration ratio range.

18. The apparatus according to claim 12, wherein the estimating component of the data processing device further has the processor to load computer instructions enabling the processor to estimate a concentration ratio of the first concentration and the second concentration from the derivative of the determined reflectance spectrum around different isosbestic wavelengths of the first absorber and the second absorber in different wavelength regions to obtain estimated concentration ratios for each one of the isosbestic wavelengths.

19. The apparatus according to claim 18, further comprising:

a comparator of the data processing device having the processor to load computer instructions enabling the processor to compare each one of the estimated concentration ratios to a predetermined concentration ratio range; and an output component of the data processing device having the processor to load computer instructions enabling the processor to indicate a defect for the surface area when at least one of the concentration ratios is outside the concentration ratio range.

20. The apparatus according to claim 18, wherein the estimating component of the data processing device further has the processor to load computer instructions enabling the processor to associate each isosbestic wavelength with a respective optical penetration depth; and the apparatus further comprising an output component of the data processing device having the processor to load computer instructions enabling the processor to indicate a defect and a depth thereof for the surface area when at least one of the concentration ratios is outside the concentration ratio range.

21. The apparatus according to claim 18, wherein the estimating component of the data processing device further has the processor to load computer instructions enabling the processor to associate each isosbestic wavelength with a respective optical penetration depth and, if small defects are to be located, to select an isosbestic wavelength among different isosbestic wavelengths with a low optical penetration depth.

22. A non-transitory storage medium storing computer instructions which, when loaded in the processor of the data processing device of claim 12 to carry out the steps of the image processing component, the calculating component and the estimating component.

23. An apparatus for determining a property of an optically diffuse medium, the medium comprising a first optical absorber having a first concentration and a second optical absorber having a second concentration, the apparatus comprising:
a light source configured to illuminate a surface area of a volume of the medium;
a spectrograph configured to receive reflected light from the surface area of the medium;
a light processing component of a data processing device having a processor to load computer instructions enabling the processor to determine the reflectance spectrum of the medium at the surface area at multiple wavelengths around an isosbestic wavelength of the first absorber and the second absorber;
a calculating component of the data processing device having the processor to load computer instructions enabling the processor to determine a derivative of the determined reflectance spectrum around the isosbestic wavelength; and
an estimating component of the data processing device having the processor to load computer instructions enabling the processor to estimate a concentration ratio ($\psi$) of the first concentration and the second concentration from the derivative of the determined reflectance spectrum around the isosbestic wavelength,
wherein the concentration ratio ($\psi$) is determined using the partial derivative of a first molar absorption coefficient of the first absorber as a function of the wavelength, and the partial derivative of a second molar absorption coefficient of the second absorber as a function of the wavelength, both taken at a wavelength at which the first molar absorption coefficient and the second molar absorption coefficient are equal.

24. The apparatus according to claim 23, further comprising:
a stage configured to support the medium; and
an actuator configured to drive the stage to move the medium relative to the optical imaging device.

25. The apparatus according to claim 23, further comprising:
a scanning device configured to transmit reflected light from different surface areas of the medium to the spectrograph.

26. The apparatus according to claim 23, wherein the concentration ratio ($\psi$) is determined as:

$$\psi = \frac{\frac{2DX}{\Delta\lambda} - \frac{\partial\mu_{a,2}}{\partial\lambda}\bigg|_{\lambda_0}}{\frac{\partial\mu_{a,1}}{\partial\lambda}\bigg|_{\lambda_0} - \frac{\partial\mu_{a,2}}{\partial\lambda}\bigg|_{\lambda_0}} = \frac{\frac{2DX}{\Delta\lambda} - g}{f - g}$$

where:
f and g are defined by $$f = \frac{\frac{\partial\mu_{a,1}}{\partial\lambda}\bigg|_{\lambda_0}}{\mu_{a,0}} \text{ and } g = \frac{\frac{\partial\mu_{a,2}}{\partial\lambda}\bigg|_{\lambda_0}}{\mu_{a,0}};$$

$\lambda$ indicates a wavelength;
$\lambda_0$ indicates an isosbestic wavelength;
$\Delta\lambda$ indicates a wavelength difference from the isosbestic wavelength;
DX indicates an imaging ratio, defined by subtracting two images taken $\Delta\lambda$ apart from an isosbestic wavelength $\lambda_0$ and dividing by the sum of the two images;
$\mu_{a,m}$ indicates a molar absorption coefficient of absorber m; and
$\mu_{a,0}$ indicates a molar absorption coefficient at isosbestic wavelength.

27. The apparatus according to claim 23, wherein the derivative of the determined reflectance spectrum around the isosbestic wavelength is a first derivative.

28. The apparatus according to claim 23, further comprising:
a comparator of the data processing device having the processor to load computer instructions enabling the processor to compare the concentration ratio ($\psi$) to a predetermined concentration ratio range; and
an output component of the data processing device having the processor to load computer instructions enabling the processor to indicate a defect for the surface area when the concentration ratio is outside the concentration ratio range.

29. The apparatus according to claim 23, wherein the estimating component of the data processing device further has the processor to load computer instructions enabling the processor to estimate a concentration ratio of the first concentration and the second concentration from the derivative of the determined reflectance spectrum around different isosbestic wavelengths of the first absorber and the second absorber in different wavelength regions to obtain estimated concentration ratios for each one of the isosbestic wavelengths.

30. The apparatus according to claim 29, further comprising:
a comparator of the data processing device having the processor to load computer instructions enabling the processor to compare each one of the estimated concentration ratios to a predetermined concentration ratio range; and
an output component of the data processing device having the processor to load computer instructions enabling the processor to indicate a defect for the surface area when at least one of the concentration ratios is outside the concentration ratio range.

31. The apparatus according to claim 29, wherein the estimating component of the data processing device further has the processor to load computer instructions enabling the processor to associate each isosbestic wavelength with a respective optical penetration depth; and
the apparatus further comprising an output component of the data processing device having the processor to load computer instructions enabling the processor to indicate a defect and a depth thereof for the surface area when at least one of the concentration ratios is outside the concentration ratio range.

32. The apparatus according to claim 29, wherein the estimating component of the data processing device further has the processor to load computer instructions enabling the processor to associate each isosbestic wavelength with a respective optical penetration depth and, if small defects are to be located, to select an isosbestic wavelength among different isosbestic wavelengths with a low optical penetration depth.

33. A non-transitory storage medium storing computer instructions which, when loaded in the processor of the data processing device of claim 23 to carry out the steps of the image processing component, the calculating component and the estimating component.

\* \* \* \* \*